United States Patent [19]

Casida et al.

[11] Patent Number: 4,965,257

[45] Date of Patent: Oct. 23, 1990

[54] PESTICIDAL COMPOUNDS

[75] Inventors: John E. Casida, Berkeley, Calif.; Christopher J. Palmer, Ipswich, England; John P. Larkin, Leighton Buzzard, England; Ian H. Smith, Eaton Bray, England

[73] Assignee: The Regents of the University of California, Berkeley, Calif.

[21] Appl. No.: 384,067

[22] Filed: Jul. 24, 1989

Related U.S. Application Data

[63] Continuation of Ser. No. 910,089, Sep. 22, 1986, abandoned, which is a continuation-in-part of Ser. No. 779,167, Sep. 23, 1985, Pat. No. 4,772,624, which is a continuation-in-part of Ser. No. 692,818, Jan. 23, 1984, abandoned, which is a continuation-in-part of Ser. No. 575,843, Jan. 30, 1984, abandoned.

[30] Foreign Application Priority Data

Sep. 24, 1985 [GB] United Kingdom ............ 8523582
Jun. 1, 1986 [GB] United Kingdom ............ 8600201
Dec. 3, 1986 [GB] United Kingdom ............ 8606131

[51] Int. Cl.$^5$ .................. A01N 57/00; A61K 31/655

[52] U.S. Cl. ............................ 514/149; 514/452; 549/214; 549/215; 549/332; 549/337; 549/360; 549/363

[58] Field of Search ............... 549/363, 214, 215, 337, 549/332, 360; 514/452, 149

[56] References Cited

U.S. PATENT DOCUMENTS 3,577,438  5/1971  Melaas ........................... 549/363
3,686,224  8/1972  Deffner .......................... 549/363

FOREIGN PATENT DOCUMENTS 0059985  4/1983  Japan .

Primary Examiner—Richard L. Raymond
Assistant Examiner—Amelia A. Owens
Attorney, Agent, or Firm—Nixon & Vanderhye

[57] ABSTRACT

Bicyclo-[2,2,1]-heptanes, bicyclo-[2,2,2]-octanes and bicyclo-[2,2,3]-nonanes, having 2 or 3 ring hetero atoms selected from O, S and N, substituted at the 1-position by a 4-alkynylphenyl group and at the 4-position and optionally at the 3 and/or 5-position are valuable pesticides, particularly insecticides and acaracides. The compounds may be prepared by reacting an alkyne with the corresponding 4-iodophenyl substituted compounds or by debromination of the corresponding 4-dibromomethylphenyl substituted compound.

9 Claims, No Drawings

PESTICIDAL COMPOUNDS

CROSS-REFERENCE

This is a continuation of application Ser. No. 06/910,089, filed Sept. 22, 1986, now abandoned, which is a continuation-in-part of co-pending application Ser. No. 779,167, filed Sept. 23, 1985, now U.S. Pat. No. 4,772,624, which is in turn a continuation-in-part application of Ser. No. 692,818, filed Jan. 23, 1984, abandoned which is in turn a continuation-in-part application of Ser. No. 575,843, filed Jan. 30, 1984, abandoned.

The present invention relates to novel chemical compounds having pesticidal activity, to methods for their preparation, to compositions containing them and to their use in the control of pests. More particularly the invention relates to a class of heterobicycloalkanes.

The use of certain 2,6,7-trioxabicyclo[2,2,2]octanes is disclosed in European patent application No. 152229. It has now been discovered that derivatives of these compounds have interesting pesticidal activity.

Accordingly the present invention provides a compound of the formula (I)

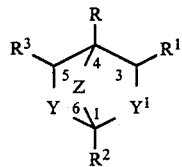

wherein

R is $C_{2-10}$ alkyl, alkenyl or alkynyl, each optionally substituted by, or methyl substituted by, cyano, halo, $C_{3-4}$ cycloalkyl $C_{1-4}$ alkoxy, or a group $S(O)_mR^4$ where $R^4$ $C_{1-4}$ alkyl and m is 0, 1 or 2, or R is $C_{3-10}$ cycloalkyl, $C_{4-10}$ cycloalkenyl or phenyl, each optionally substituted by $C_{1-4}$ alkoxy, $C_{1-3}$ alkyl, $C_{2-4}$ alkynyl, halo, cyano or a group $S(O)_mR^4$ as defined hereinbefore;

$R^1$ and $R^3$ may be the same or different, and is hydrogen, halo, $C_{1-3}$ alkyl, $C_{2-3}$ alkenyl or alkynyl, the alkyl, alkenyl or alkynyl each being optionally substituted by halo, cyano, or $C_{1-4}$ alkoxy; alkyl carbalkoxy containing up to 6 carbon atoms, a group $S(O)_mR^4$ as defined hereinbefore or alkynyl substituted by tri-$C_{1-4}$ alkylsilyl, or $R^1$ is $COO-C_{1-4}$-alkyl, cyano, gem dimethyl, gem di-cyano, gem-dihalo, gem di-ethynyl, spiro-cyclopropyl, spiro-oxirane or spiro-oxetane, substituted spiro oxirane or spiro-oxetane, oxo or methylene optionally substituted by cyano, halo or trifluoromethyl or $R^1$ and R and the carbon atoms to which they are attached form a $C_{5-7}$ carbocyclic ring optionally $R^2$ is a phenyl group substituted at the 4-position by a group $-(C\equiv C)_nR^5$ and optionally substituted at other positions of the phenyl ring, wherein n is 1 or 2, $R^5$ is hydrogen, bromine, chlorine, iodine, a group $S(O)_mR^{4x}$ wherein $R^{4x}$ is trifluoromethyl or a group $R^4$ and m and $R^4$ are as hereinbefore defined, an optionally substituted aliphatic or cycloaliphatic group containing up to 9 carbon atoms, a group $-CX.R^6$ where X is oxygen or sulphur and $R^6$ is a $C_{1-6}$ hydrocarbyl or hydrocarbyloxy group optionally substituted by fluoro or an amino group optionally substituted by one or two $C_{1-4}$ alkyl groups or $R^5$ is cyano, or a silyl group substituted by three $C_{1-4}$ alkyl groups or two $C_{1-4}$ alkyl groups and a phenyl group;

Y and $Y^1$ are the same or different and are each selected from oxygen and $S(O)_m$ where m is 0, 1 or 2; Z is $CH_2CH_2$, $CH_2CH_2O$, sulphur, $CH_2O$, $CH_2S$, $CHR^{1x}NR^7$ wherein $R^{1x}$ is hydrogen, cyano, halo, a group $CO_2R^4$ or $C_{1-3}$ alkyl, $C_{2-3}$ alkenyl or alkynyl each optionally substituted by halo, cyano, $C_{1-4}$ alkoxy, alkyl carbalkoxy containing up to 6 carbon atoms or a group $S(O)_mR^4$ wherein m and $R^4$ are as hereinbefore defined and $R^7$ is hydrogen, benzyl, $C_{1-4}$ alkyl, $C(O) R^8$ wherein $R^8$ is $C_{1-4}$ alkyl, alkoxy or a group $NHR^9$ wherein $R^9$ is $C_{1-4}$ alkyl, $C_{7-8}$ aralkyl or phenyl optionally substituted by halo or Z is $-CO.CH_2-$ or $-CH(OR^{10})CH_2$-wherein $R^{10}$ is hydrogen, $C_{1-4}$ alkyl, $C_{1-4}$ acyl or $C_{1-3}$ carbamoyl, except that when $R^5$ is hydrogen or a silyl group substituted by three alkyl groups and Y and $Y^1$ are oxygen and Z is $CH_2O$, then $R^1$ and $R^3$ must be hydrogen.

In the definition of Z, the first mentioned atom is adjacent to the 4-position of the bicyclic ring system.

Suitably R is propyl, butyl, pentyl, $C_{2-5}$ alkenyl or alkynyl, $C_{5-7}$ cycloalkyl or phenyl each optionally substituted by fluoro, chloro or bromo. Most suitably R is n-propyl, n-butyl, i-butyl, sec-butyl, t-butyl, cyclopentyl or cyclohexyl and preferably R is n-propyl, n-butyl, i-butyl or cyclohexyl.

Suitably $R^1$ is hydrogen, cyano, methyl or ethyl each optionally substituted by cyano, methoxy, methylthio, chloro, bromo or fluoro. Most suitably $R^1$ is hydrogen, methyl, cyano, trifluoromethyl or ethyl. Preferably $R^1$ is hydrogen, methyl, cyano or trifluoromethyl.

Suitable substituents on the phenyl group in $R^2$ include halo, cyano, azido, nitro, $C_{1-3}$ alkyl or alkoxy each optionally substituted by halo, or $C_{2-3}$ alkenyl or alkynyl each optionally substituted by halo. Preferably the halo substituent will be fluoro, chloro or bromo. Suitably there are up to two substituents which are preferably at the 3-and/or 5-positions, but fluoro may also be at the 2-and/or 6-positions.

Suitably $R^3$ is hydrogen, methyl or trifluoromethyl. Most suitably $R^3$ is hydrogen.

Preferably n is 1.

Suitably $R^5$ is hydrogen, optionally substituted methyl or ethyl, cyano, tri $C_{1-4}$ alkyl silyl or a group $COR^6$ wherein $R^6$ is $C_{1-4}$ alkyl or alkoxy or amino optionally substituted by one or two $C_{1-4}$ alkyl groups. Suitable substituents when $R^5$ is methyl or ethyl include hydroxy, a group $OSO_2R^{10x}$ wherein $R^{10x}$ is $C_{1-4}$ alkyl, phenyl or tolyl, $C_{1-4}$ alkoxy, $C_{1-4}$ acyloxy optionally substituted by an amino group mono or di substituted by $C_{1-4}$ alkyl groups or mono-substituted by phenyl optionally substituted by one to three halogen atoms, a group $SCOR^4$ or $S(O)_mR^4$ wherein m and $R^4$ are as hereinbefore defined or a group $NR^{11}R^{12}$ wherein $R^{11}$ is hydrogen or $C_{1-4}$ alkyl, $R^{12}$ is hydrogen, $C_{1-4}$ alkyl or a group $COR^{13}$ wherein $R^{13}$ is $C_{1-4}$ alkyl or alkoxy or $NR^{11}R^{12}$ is a five or six membered heterocyclic ring. Most suitably $R^5$ is hydrogen, trimethylsilyl or substituted methyl or substituted ethyl, the substituents being hydroxy or methoxy.

Suitably Z is $-CH_2S-$, $-CH_2O-$ or $-CH_2CH_2-$. Preferably Z is $-CH_2S-$ or $-CH_2O-$.

Suitably Y and $Y^1$ are both oxygen.

One group of compounds of the formula is that of the formula (IA):

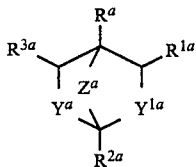

(IA)

halogen or cyano; $R^{1a}$ is hydrogen, $C_{1-3}$ alkyl, $C_{2-3}$ alkenyl or alkynyl each optionally substituted by cyano, $C_{1-4}$ alkoxy, $C_{1-4}$ alkylthio, alkyl carbalkoxy containing up to 6 carbon atoms or halo, or $R^{1a}$ is cyano, gem dimethyl or $R^{1a}$ and $R^a$ and the carbon atoms to which they are attached form a $C_{5-7}$ carbocyclic ring optionally substituted by $C_{1-3}$ alkyl, or $C_{2-3}$ alkoxy or alkenyl; $R^{2a}$ is a phenyl group substituted at the 4-position by a group —C≡C—$R^{5a}$ and optionally substituted at other positions of the phenyl ring, wherein $R^{5a}$ is an optionally substituted $C_{1-9}$ aliphatic group, —CO.$R^{6a}$ is a $C_{1-6}$ hydrocarbyl or hydrocarbyloxy group or an amino group optionally substituted by one or two $C_{1-4}$ alkyl groups or $R^{5a}$ is cyano, or a silyl group substituted by three $C_{1-4}$ alkyl groups or two $C_{1-4}$ alkyl groups and a phenyl group; and $R^{3a}$ is hydrogen, $C_{1-3}$ alkyl, $C_{2-3}$ alkenyl or alknyl each optionally substituted by cyano, $C_{1-4}$ alkylthio, $C_{1-4}$ alkoxy or halo; $Y^a$ and $Y^{1a}$ are the same or different and are each selected from oxygen or $S(O)_m$ where m is 0, 1 or 2; $Z^a$ is $CH_2CH_2$, $CH_2CH_2O$, sulphur, $CH_2O$, $CH_2S$ or $CH_2S$ or $CH_2NR^{7a}$ wherein $R^{7a}$ is hydrogen, benzyl, $C_{1-4}$ alkyl, $C(O) R^{8a}$ wherein $R^{8a}$ is $C_{1-4}$ alkyl or alkoxy, or Z is —CO.$CH_2$— or —$CH(OR^{10a})CH_2$— wherein $R^{10a}$ is hydrogen, $C_{1-4}$ alkyl $C_{1-4}$ acyl or $C_{1-3}$ carbamoyl.

Suitably $R^a$ is propyl, butyl, pentyl, $C_{2-5}$ alkenyl or alkynyl, $C_{5-7}$ cycloalkyl or phenyl each optionally substituted by fluoro, chloro or bromo. Most suitably $R^a$ is is n-propyl, i-butyl, sec-butyl, t-butyl, cyclopentyl or cyclohexyl and preferably R is n-propyl, i-butyl, t-butyl or cyclohexyl.

Suitably $R^{1a}$ is hydrogen, cyano, methyl or ethyl each optionally substituted by cyano, methoxy, methylthio, chloro, bromo or fluoro. Most suitably $R^{1a}$ is hydrogen, methyl, trifluoromethyl or ethyl. Preferably $R^{1a}$ is hydrogen, methyl or trifluoromethyl Suitable substituents on the phenyl group in $R^{2a}$ include halo, cyano, azido, nitro, $C_{1-3}$ alkyl or alkoxy each optionally substituted by halo, or $C_{2-3}$ alkenyl or alkynyl each optionally substituted by halo. Preferably the halo substituent will be fluoro, chloro or bromo. Suitably there are up to two substituents which are preferably at the 3-and/or 5-positions.

Suitably $R^{3a}$ is hydrogen, methyl or trifluoromethyl. Most suitably $R^{3a}$ is hydrogen.

Suitably $R^{5a}$ is an optionally substituted methyl or ethyl group or a cyano or tri $C_{1-4}$ alkyl silyl group or a group $COR^{6a}$ wherein $R^{6a}$ is $C_{4-4}$ alkyl or alkoxy or amino optionally substituted by one or two $C_{1-4}$ alkyl groups. Suitable substituents when $R^{5a}$ is methyl or ethyl include hydroxy, $C_{1-4}$ alkoxy, $C_{1-4}$ acyloxy, $C_{1-4}$ alkylthio or a group $NR^{11a}R^{12a}$ wherein $R^{11a}$ is hydrogen or $C_{1-4}$ alkyl, $R^{12a}$ is hydrogen, $C_{1-4}$ alkyl or a group $COR^{11a}$ wherein $R^{11a}$ is as hereinbefore defined or $NR^{11a}R^{12a}$ is a five or six membered heterocyclic ring. Most suitably $R^{5a}$ is methyl or ethyl substituted by hydroxy or methoxy or trimethylsilyl.

Suitably $Z^a$ is —$CH_2S$—, —$CH_2O$— or —$CH_2CH_2$—. Preferably Z is —$CH_2S$— or —$CH_2O$—, the heteroatom being adjacent to the carbon atom substituted by $R^{2a}$.

Suitably $Y^a$ and $Y^{1a}$ are both oxygen.

Preferred compounds of the present invention include

1-[3-nitro-4-(2-trimethylsilylethynyl)phenyl]-4-n-propyl-2,6,7-trioxabicyclo[2,2,2]octane 1-(4-ethynylphenyl)-4-n-propyl-2,6,7-trioxabicyclo[2,2,2]octane 4-n-butyl-1-(4-ethynylphenyl)-2,6,7-trioxabicyclo[2,2,2]octane 4-i-butyl-1-(4-ethynylphenyl)-2,6,7-trioxabicyclo[2,2,2]octane 1-(4-ethynylphenyl)-4-n-pentyl-2,6,7-trioxabicyclo[2,2,2]octane 4-n-pentyl-1-[4-(2-trimethylsilylethynyl)phenyl]-2,6,7trioxabicyclo[2,2,2]octane 1-[3-chloro-4-(2-trimethylsilylethynyl)phenyl]-4-n-propyl-2,6,7-trioxabicyclo[2,2,2]octane 4-propyl-1-[4-(2-trimethylsilylethynyl)phenyl]-2,6,7-trioxabicyclo[2,2,2]octane 1-[4-3-methoxyprop-1-ynyl)phenyl]-4-propyl-2,6,7-trioxabicyclo[2,2,2]octane 4-n-butyl-1-[4-(2-trimethylsilylethynyl)phenyl]-2,6,7-trioxabicyclo[2,2,2]octane 4-i-butyl1-[4-(2-trimethylsilylethynyl)phenyl]-2,6,7-trioxabicyclo[2,2,2]octane 1-[4-(3-ethoxyprop-1-ynyl)phenyl]-4-n-propyl-2,6,7-trioxabicyclo[2,2,2]octane 4-methoxy-1-[4-(4-n-propyl-2,6,7-trioxabicyclo[2,2,2]oct-1-)phenyl]but-1-yne 4-i-butyl-1-[4-(3-methoxyprop-1-ynyl-phenyl]-2,6,7-trioxabicyclo[2,2,2]octane N-[3-[4-n-propyl-2,6,7-trioxabicyclo[2,2,2]oct-1-yl)phenyl]prop-2-ynyl acetamide 4-(2,2-di-methylpropyl)-1-(4-ethynylphenyl)-2,6,7-trioxabicyclo[2,2,2]octane methyl 3-[4-(4-n-propyl-2,6,7-trioxabicyclo[2,2,2]oct-1-yl)phenyl]prop-2-ynoate 1-(3-chloro-4-ethynylphenyl)-4-n-propyl-2,6,7-trioxabicyclo[2,2,2]octane 1-(4-ethynyl-3-nitrophenyl)-4-n-propyl-2,6,7-trioxabicyclo[2,2,2]octane 4-t-butyl-1-(4-ethynylphenyl)-2,6,7-trioxabicyclo[2,2,2]octane 4-cyclohexyl-1-(4-ethynylphenyl)-2,6,7-trioxabicyclo[2,2,2]octane 4-t-butyl-1-[4-(3-methoxyprop-1-ynyl)phenyl]-2,6,7-trioxabicyclo[2,2,2]octane 4-t-butyl-1-(4-ethynylphenyl)-2,6,7-trioxabicyclo[2,2,2]octane 4-cyclohexyl-1-(4-ethynylphenyl)-2,6,7-trioxabicyclo[2,2,2]octane 4-t-butyl-1-[4-(3-methoxyprop-1-ynyl)phenyl]-2,6,7-trioxabicyclo[2,2,2]octane 4-cyclohexyl-1-[4-(2-trimethylsilylethynyl)phenyl]-2,6,7-trioxabicyclo[2,2,2]octane 4-ethyl-1-(4-ethynylphenyl)-2,6,7-trioxabicyclo[2,2,2]octane 4-t-butyl-1-[4-(2-trimethylsilylethynyl)phenyl]-2,6,7-trioxabicyclo[2,2,2]octane 1-[3-chloro-4-(3-methoxyprop-1-ynyl)phenyl]-4-n-propyl-2,6,7-trioxabicyclo[2,2,2]octane 4-cyclohexyl-1-[4-(3-methoxyprop-1-ynyl)phenyl]2,6,7-trioxabicyclo[2,2,2]octane 4-n-butyl-1-[4-(3-methoxyprop-1-ynyl)phenyl]2,6,7-trioxabicyclo[2,2,2]octane 1-[4-(3-methoxyprop-1-ynyl)phenyl]-4-n-pentyl-2,6,7-trioxabicyclo[2,2,2]octane
1-[4-(3-methoxyprop-1-ynyl)phenyl]-4-n-propyl-3-trifluoromethyl-2,6,7-trioxabicyclo[2,2,2]octane
3-cyano-1-[4-(3-methoxyprop-1-ynyl)phenyl]-4-n-propyl-2,6,7-trioxabicyclo[2,2,2]octane
4-(2,2-dimethylpropyl)-1-[4-(3-methoxyprop-1-yl)-phenyl]-2,6,7-trioxabicyclo [2,2,2]octane
4-(2,2-dimethylpropyl)-1-[4-(2-trimethylsilylethynyl)-phenyl]-2,6,7-trioxabicyclo [2,2,2]octane
N-methyl-3-[4-n-(4-propyl-2,6,7-trioxabicyclo[2,2,2]oct-1-yl)phenyl]prop-2-ynyl carbamate
3-[4-(4-n-propyl-2,6,7-trioxabicyclo[2,2,2]octyl)-phenyl]prop-2-yn-1-ol
3-[4-(4-n-propyl-2,6,7-trioxabicyclo[2,2,2]oct-1-yl)phenyl]prop-2-ynyl acetate
4-n-propyl-1-[4-(prop-1-ynyl)-phenyl]-2,6,7-trioxabicyclo[2,2,2]octane
1-[4-(3-methoxyprop-1-ynyl)-phenyl4-n-propyl-2,6,-dioxa-7-thiabicyclo[2,2,2]octane
1-[4-(2-t-butyldimethylsilylethynyl)phenyl]-4-n-propyl-2,6,7-trioxabicyclo [2,2,2]octane
3-[4-(4-n-propyl-2,6,7-trioxabicyclo[2,2,2]oct-1-yl)phenyl]prop-2-ynyl-methanesulphonate
N-methyl-3-(4-(4-n-propyl-2,6,7-trioxabicyclo[2,2,-2]oct-2-yl)phenyl]-prop-2-ynamide
N-methyl-3-(4-(4-n-propyl-2,6,7-trioxabicyclo[2,2,-2]oct-1-yl)phenyl]-prop-2-ynthioamide
4-n-butyl-1-[4-(3-methoxyprop-1-ynyl)phenyl]-3-trifluoromethyl-2,6,7-trioxabicyclo [2,2,2]octane
1-[4-(pent-1-ynyl)phenyl]-4-n-propyl-2,6,7-trioxabicyclo[2,2,2]octane
1-(4-ethynylphenyl)-4-phenyl-2,6,7-trioxabicyclo[2,2,-2]octane
4-Phenyl-1-[4-(2-trimethylsilylethynylphenyl)]-2,6,7-trioxabicyclo[2,2,2]octane
4-n-propyl-1-[4-(2-trimethylsilylethynylphenyl)]-2,6-dioxa-7-thiabicyclo[2,2,2]octane
1-(4-ethynylphenyl)-4-n-propyl-2,6-dioxa-7-thiabicyclo[2,2,2]octane By the term "hydrocarbyl" group is meant alkyl, alkenyl (including cyclic alkyl and alkenyl, and alkyl and alkenyl substituted by cyclic alkyl and alkenyl), alkynyl, aryl and aralkyl groups. "Hydrocarbyloxy" means a hydrocarbyl group as defined where linked to oxygen.

In a further aspect, the present invention provides a process for the preparation of a compound of the formula (I). The process for the preparation of a compound of the formula (I) may be any method known in the art for preparing analogous compounds, for example:

(i) by the reaction of the corresponding compound which contains iodo in place of —C≡C—$R^5$ with a compound HC≡C$R^5$ wherein $R^5$ is as hereinbefore defined. This reaction is carried out in the presence of a suitable palladium catalyst well known to those skilled in the art for this type of reaction, for example bistriphenylphosphine palladium dichloride, and a catalytic amount of a cuprous halide, such as cuprous iodide. The reaction will normally be carried out in the presence of basic solvent such as diethylamine or triethylamine at a non-extreme temperature, for example between −50° and 100° C. and conveniently at room temperature. The starting material, i.e. the iodophenylbicycloalkane, wherein Y and $Y^1$ are oxygen and Z is $CH_2O$ may be prepared by the cyclisation of a compound of the formula (II);

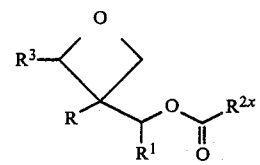

wherein R, $R^1$ and $R^3$ are as hereinbefore defined and $R^{2x}$ is an iodo substituted phenyl group, in the presence of an acid catalyst. Boron trifluoride etherate is a particularly preferred acid catalyst for this cyclisation which will normally be carried out in an inert solvent, such as a halogenated hydrocarbon, conveniently dichloromethane, at below ambient temperature, for example between −100 and 0° C. and conveniently between −70 and −50° C.

The compounds of the formula (II) may be prepared by the reaction of compounds of the formula (III) and (IV):

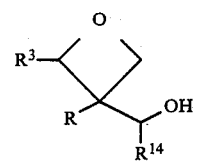

where $R^{14}$ is a group $R^1$ and R, $R^1$, $R^{2x}$ and $R^3$ are as hereinbefore defined and L is leaving group such as halo. This reaction conveniently takes place in an inert solvent in the presence of base at a non-extreme temperature. Halogenated hydrocarbons, such as dichloromethane are particularly suitable solvents, pyridine is a preferred base and the reaction will conveniently be carried out at between −50 and 100° C., preferably at 0° C.

The compounds of the formula (III) may in turn be prepared from compounds of the formula (V):

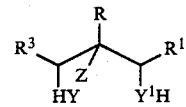

wherein R, $R^1$ and $R^3$ are as defined above and Y and $Y^1$ are oxygen and Z is $CH_2OH$, by reaction with diethyl carbonate in the presence of a strong base, for example potassium hydroxide, in a polar solvent, such as an alcohol, for example ethanol, at an elevated temperature, for example between 50 and 100° C. This is a preferred method of making compounds of the formula (III) wherein $R^{14}$=$CF_3$ The compounds of the formula (III) may alternatively be prepared by the reaction of a Grignard reagent $R^1$MgHal with a compound of the formula (VI)

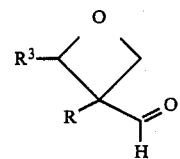

wherein R, $R^1$ and $R^3$ are as hereinbefore defined and Hal is a halogen atom such as bromine or iodine. This reaction is conveniently carried out in an inert solvent, suitably an ether for example diethyl ether, at a non-extreme temperature, for example between $-50$ and $50°$ C. and preferably between $-10°$ and $10°$ C. The compounds of the formula (VI) may be prepared by oxidation of compounds of the formula (III) wherein $R^{14}$ is hydrogen by using oxalyl chloride and dimethyl sulphoxide in an inert solvent, such as a halogenated hydrocarbon, for example dichloromethane, followed by a base such as triethylamine or by using pyridinium chlorochromate in an inert solvent, such as a halogenated hydrocarbon, for example dichloromethane.

The compounds of the formula (III) wherein $R^{14}$ is hydrogen may be prepared from compounds of formula (V) in an analogous manner to the preparation of the compounds of the formula (III) where $R^{14}$ is trifluoromethyl.

The triol of the formula (V) may be prepared:

(i) In certain cases, it may be convenient to prepare triol derivatives where $R^1$, $R^3$ are hydrogen and one of the hydroxy groups is protected, by reduction of an ester of the formula (VII):

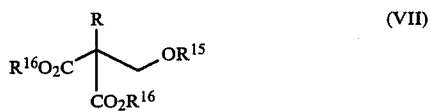

(VII)

wherein $R^{15}$ is a hydroxy protecting group such as benzyl and $R^{16}$ is $C_{1-4}$ alkyl. This reduction is suitably carried out by a complex hydride such as lithium aluminium hydride in an inert solvent conveniently an ether. The compound of the formula (VII) may be prepared from the corresponding compound $RCH(CO_2R^{16})_2$ by reaction with a compound $XCH_2OR^{15}$, wherein X is a leaving group such as a halogen, in the presence of a strong base, such as sodium hydride.

(ii) when it is required to prepare a compound of the formula (I) wherein $R^3$ is hydrogen, by the reduction of a compound of the formula (VIII):

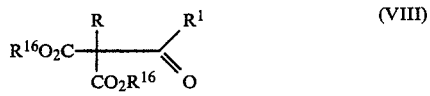

(VIII)

wherein R, $R^1$ and $R^{16}$ are as hereinbefore defined. This reduction is suitably carried out by means of a complex hydride, such as lithium aluminum hydride in an inert solvent such as an ether, for example diethyl ether.

When R and $R^1$ are linked to form a carbocyclic ring, the compound of the formula (VIII) is conveniently prepared by the reaction of a compound of the formula (IX)

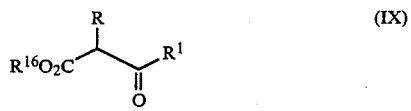

(IX)

with a compound hal—$CO_2R^{16}$, wherein R, $R^1$ and $R^{16}$ are as hereinbefore defined and hal is halogen, for example chlorine. This reaction is conveniently carried out in the presence of a Grignard reagent for example ethyl magnesium bromide, in an inert solvent such as an ether, for example tetrahydrofuran. Other compounds of the formula (VIII) are conveniently prepared by the reaction of a compound $RCH(CO_2R^{16})_2$ with a compound hal $CO.R^1$ wherein R, $R^1$, $R^{16}$ and hal are as hereinbefore defined or trifluoroacetic anhydride. This reaction is conveniently carried out in the presence of a strong base, such as a metal hydride in a non-polar solvent, for example an aromatic hydrocarbon such as benzene or toluene.

The compounds which contain iodo in place of —C≡C—$R^5$ may also be prepared from the corresponding bromo compound. This reaction proceeds by the reaction of the bromo compound with an alkyllithium compound, for example n-butyllithium, in an inert solvent, such as an ether, conveniently diethyl ether, at a non-extreme temperature, for example between $-80°$ and $20°$ C. and conveniently between $-70$ and $0°$ C., to give the corresponding lithium intermediate which is then reacted with iodine in an inert solvent such as an ether, conveniently diethyl ether. The reaction sequence is conveniently carried out in situ, the organo lithium intermediate not being isolated.

The bromo-compound may be prepared by the cyclisation of a compound of the formula (II) wherein $R^{2x}$ is a bromosubstituted phenyl group under the conditions previously described for the corresponding iodo compound. Alternatively, it may be prepared by the reaction of a compound analogous to that of the formula (V) and wherein R, $R^1$, $R^3$, Y, $Y^1$ and Z are as defined in relation to formula (I) with an orthocarboxylate of the formula $R^{2x}$ $C(OR^{17})_3$ wherein $R^{2x}$ is a bromosubstituted phenyl group and $R^{17}$ is $C_{1-4}$ alkyl, phenyl or $C_{7-8}$ aralkyl. Suitably $R^{17}$ is methyl or ethyl, preferably methyl. The reaction is normally carried out in the presence of an acid such as a mineral acid, conveniently hydrochloric acid or a sulphonic and derivative, such as toluene sulphonic acid, or an acid resin, or in the presence of a trialkylamine, such as triethylamine, at an elevated temperature, for example between 50 and 200° C., conveniently between 120 and 170° C. The reaction may conveniently be carried out in the absence of a solvent but a suitable solvent may be added if desired. The preparation of such bromophenylsubstituted bicyclooctanes is described in European patent application Nos. 152229 and 86305820 and UK patent application Nos. 8523582 and 8600201 which are incorporated by reference herein.

(ii) The compounds of the formula (I) wherein $R^5$ is hydrogen may also be prepared by dehydrobromination of the corresponding 1,2-bromoethyl compound, i.e. a compound wherein $R^2$ is replaced by a (1,2-bromoethyl)phenyl group. This reaction is conveniently carried out in the presence of sodamide in liquid ammonia. The reaction may be carried out in an inert solvent, such as an ether, for example tetrahydrofuran at a non-extreme temperature, for example between $-20$ and $50°$ C. and conveniently at room temperature.

(iii) It is often convenient to prepare compounds of the formula (I) by interconversion from other compounds of the formula (I), for example:

(i): when it is desired to prepare a compound of the formula (I) wherein $R^5$ is other than hydrogen by the reaction of the corresponding compound wherein $R^5$ is hydrogen with a compound Hal $R^5$ wherein hal is halogen and $R^5$ is other than hydrogen. This reaction is particularly suitable for the preparation of those compounds wherein $R^5$ is a $C_{1-4}$ alkyl group or a group $COR^6$ wherein $R^6$ is a $C_{1-6}$ alkoxy group. The reaction is normally carried out in the presence of a strong base, such as an alkyllithium conveniently butyllithium in an inert solvent, such as an ether, for example tetrahydrofuran, at a non-extreme temperature, for example between $-50°$ and $50°$ C. and conveniently between $-10$ and $30°$ C. The starting material, i.e. the unsubstituted alkynylphenyl bicycloalkane may be prepared as described above.

(ii) when it is desired to prepare a compound of the formula (I) wherein $R^5$ is hydrogen by the desilylation of a compound of the formula (I) wherein $R^5$ is a tri—$C_{1-4}$ alkylsilyl group. This reaction may be carried out by methods well known to those skilled in the art, for example by reaction with tetrabutyl-ammonium fluoride in an ether, such as tetrahydrofuran, at a non-extreme temperature, for example between $0°$ and $70°$ C. and conveniently at room temperature.

The compounds of Formula (I) may be used to control arthropods such as insect and acarine pests. Thus, the present invention provides a method for the control of arthropods which comprises administering to the arthropod or to its environment on arthropodically effective amount of a compound of the formula (I). The present invention also provides a method for the control and/or eradication of arthropod infestations on animals (including humans) which comprises administering to the animal an effective amount of a compound of the formula (I). The present invention further provides for the compounds of the formula (I) for use in human and veterinary medicine for the control of arthropod pests.

The compounds of Formula (I) may be used for such purposes by application of the compounds themselves or in diluted form in known fashion as a dip, spray, lacquer, foam, dust, powder, aqueous suspension, paste, gel, shampoo, grease, combustible solid, vapourising mat, combustible coil, bait, wettable powder, granule, aerosol, emulsifiable concentrate, oil suspensions, oil solutions, pressure-pack, impregnated article or pour on formulation. Dip concentrates are not applied per se, but diluted with water and the animals immersed in a dipping bath containing the dip wash. Sprays may be applied by hand or by means of a spray race or arch. The animal, plant or surface being treated may be saturated with the spray by means of high volume application or superficially coated with the spray by means of light or ultra low volume application. Aqueous suspensions may be applied in the same manner as sprays or dips. Dusts may be distributed by means of a powder applicator or, in the case of animals, incorporated in perforated bags attached to trees or rubbing bars. Pastes, shampoos and greases may be applied manually or distributed over the surface of an inert material against which animals rub and transfer the material to their skins. Pour-on formulations are dispensed as a unit of liquid of small volume on to the backs of animals such that all or most of the liquid is retained on the animals.

The compounds of Formula (I) may be formulated either as formulations ready for use on the animals, plants or surface or as formulations requiring dilution prior to application, but both types of formulation comprise a compound of Formula (I) in intimate admixture with one or more carriers or diluents. The carriers may be liquid, solid or gaseous or comprise mixtures of such substances, and the compound of Formula (I) may be present in a concentration of from 0.025 to 99% w/v depending upon whether the formulation requires further dilution.

Dusts, powder and granules comprise the compound of Formula (I) in intimate admixture with a powdered solid inert carrier for example suitable clays, kaolin, talc, mica, chalk, gypsum, vegetable carriers, starch and diatomaceous earths.

Sprays of a compound of Formula (I) may comprise a solution in an organic solvent (e.g. those listed below) or an emulsion in water (dip wash or spray wash) prepared in the field from an emulsifiable concentrate (otherwise known as a water miscible oil) which may also be used for dipping purposes. The concentrate preferably comprises a mixture of the active ingredient, with or without an organic solvent and one or more emulsifiers. Solvents may be present within wide limits but preferably in an amount of from 0 to 90% w/v of the composition and may be selected from kerosene, ketones, alcohols, xylene, aromatic naphtha, and other solvents known in the formulating art. The concentration of emulsifiers may be varied within wide limits but is preferably in the range of 5 to 25% w/v and the emulsifiers are conveniently non-ionic surface active agents including polyoxyalkylene esters of alkyl phenols and polyoxyethylene derivatives of hexitol anhydrides and anionic surface active agents including Na lauryl sulphate, fatty alcohol ether sulphates, Na and Ca salts of alkyl aryl sulphonates and alkyl sulphosuccinates.

Wettable powders comprise an inert solid carrier, one or more surface active agents, and optionally stabilisers and/or anti-oxidants.

Emulsifiable concentrates comprise emulsifying agents, and often an organic solvent, such as kerosene, ketones, alcohols, xylenes, aromatic naphtha, and other solvents known in the art.

Wettable powders and emulsifiable concentrates will normally contain from 5 to 95% by weight of the active ingredient, and are diluted, for example with water, before use.

Lacquers comprise a solution of the active ingredient in an organic solvent, together with a resin, and optionally a plasticiser.

Dip washes may be prepared not only from emulsifiable concentrates but also from wettable powders, soap based dips and aqueous suspensions comprising a compound of Formula (I) in intimate admixture with a dispersing agent and one or more surface active agents.

Aqueous suspensions of a compound of Formula (I) may comprise a suspension in water together with suspending, stabilizing or other agents. The suspensions or solutions may be applied per se or in a diluted form in known fashion.

Greases (or ointments) may be prepared from vegetable oils, synthetic esters of fatty acids or wool fat together with an inert base such as soft paraffin. A compound of Formula (I) is preferably distributed uniformly through the mixture in solution or suspension. Greases may also be made from emulsifiable concentrates by diluting them with an ointment base.

Pastes and shampoos are also semi-solid preparations in which a compound of Formula (I) may be present as an uniform dispersion in a suitable base such as soft or liquid paraffin or made on a non-greasy basis with glycerin, mucilage or a suitable soap. As greases, shampoos and pastes are usually applied without further dilution they should contain the appropriate percentage of the compound of Formula (I) required for treatment.

Aerosol sprays may be prepared as a simple solution of the active ingredient in the aerosol propellant and co-solvent such as halogenated alkanes and the solvents referred to above, respectively. Pour-on formulations may be made as a solution or suspension of a compound of Formula (I) in a liquid medium. An avian or mammal host may also be protected against infestation of acarine ectoparasites by means of carrying a suitably-moulded, shaped plastics article impregnated with a compound of Formula (I). Such articles include impregnated collars, tags, bands, sheets and strips suitably attached to appropriate parts of the body. Suitably the plastics material is a polyvinyl chloride (PVC).

The concentration of the compound of Formula (I) to be applied to an animal will vary according to the compound chosen, the interval between treatments, the nature of the formulation and the likely infestation, but in general 0.001 to 20.0% w/v and preferably 0.01 to 10% of the compound should be present in the applied formulation. The amount of the compound deposited on an animal will vary according to the method of application, size of the animal, concentration of the compound in the applied formulation, factor by which the formulation is diluted and the nature of the formulation but in general will lie in the range of from 0.0001% to 0.5% except for undiluted formulations such as pour-on formulations which in general will be deposited at a concentration in the range from 0.1 to 20.0% and preferably 0.1 to 10%.

The compounds of formula (I) are also of use in the protection and treatment of plant species, in which case an effective insecticidal or acaricidal amount of the active ingredient is applied. The application rate will vary according to the compound chosen, the nature of the formulation, the mode of application, the plant species, the planting density and likely infestation and other like factors but in general, a suitable use rate for agricultural crops is in the range 0.001 to 3 kg/Ha and preferably between 0.01 and 1 kg/Ha. Typical formulations for agricultural use contain between 0.0001% and 50% of a compound of formula (I) and conveniently between 0.1 and 15% by weight of a compound of the formula (I).

Particular crops include cotton, wheat, maize, rice, sorghum, soya, vines, tomatoes, potatoes, fruit trees and spruce.

Dusts, greases, pastes and aerosol formulations are usually applied in a random fashion as described above and concentrations of 0.001 to 20% w/v of a compound of Formula (I) in the applied formulation may be used.

The compounds of formula (I) have been found to have activity against the common housefly (*Musca domestica*). In addition, certain compounds of formula (I) have activity against other arthropod pests including *Tetranychus urticae Plutella xylostella*, Culex spp. and *Blattella germanica*) The compounds of formula (I) are thus useful in the control of arthropods e.g. insects and acarines in any environment where these constitute pests, e.g. in agriculture, in animal husbandry, in public health control and in domestic situations.

Insect pests include members of the orders Coleoptera (e.g. Anobium, Tribolium, Sitophilus, Diabrotica, Anthonomus or Anthrenus spp.), Lepidoptera (e.g. Ephestia, Plutella, Chilo, Heliothis, Spodoptera or Tineola spp.), Diptera (e.g. Musca, Aedes, Culex, Glossina, Stomoxys, Haematobia, Tabanus, Hydrotaea, Lucilia, Chrysomia, Callitroga, Dermatobia, Hypoderma, Liriomyza and Melophagus spp.), Phthiraptera (Malophaga e.g. Damalina spp. and Anoplura e.g. Linognathus and Haematopinus spp.), Hemiptera (e.g. Aphis, Bemisia, Aleurodes, Nilopavata, Nephrotetix or Cimex spp.), Orthoptera (e.g. Schistocerca or Acheta spp.), Dictyoptera (e.g. Blattella, Periplaneta or Blatta spp.), Hymenoptera (e.g. Solenopsis or Monomorium spp.), Isoptera (e.g. Reticulitermes spp.), Siphonaptera (e.g. Ctenocephalides or Pulex spp.), Thysanura (e.g. Lepisma spp.), Dermaptera (e.g. Forficula spp.) and Pscoptera (e.g. Peripsocus spp.).

Acarine pests include ticks, e.g. members of the genera Boophilus, Rhipicephalus, Amblyomma, Hyalomma, Ixodes, Haemaphysalis, Dermocentor and Anocentor, and mites and manges such as Tetranychus, Psoroptes, Notoednes, Psorergates, Chorioptes and Demodex spp.

Compounds of the invention may be combined with one or more other active ingredients (for example pyrethroids, carbamates and organophosphates) and/or with attractants and the like. Furthermore, it has been found that the activity of the compounds of the invention may be enhanced by the addition of a synergist or potentiator, for example: one of the oxidase inhibitor class of synergists, such as piperonyl butoxide or propyl 2-propynylphenylphosphonate; a second compound of the invention; or a pyrethroid pesticidal compound. When an oxidase inhibitor synergist is present in a formula of the invention, the ratio of synergist to compound of Formula (I) will be in the range 25:1–1:25 eg about 10:1.

Stabilisers for preventing any chemical degradation which may occur with the compounds of the invention include, for example, antioxidants (such as tocopherols, butylhydroxyanisole and butylhydroxytoluene) and scavengers (such as epichlorhydrin) and organic or inorganic bases e.g. trialkylamines such as triethylamine which can act as basic stabilises and as scavengers.

The following Examples illustrate, in a non-limiting manner, preferred aspects of the invention. All temperatures are in degrees Celsius.

EXAMPLE 1

4-Ethyl-1-[4-(2-trimethylsilylethynyl)-phenyl]-2,6,7-trioxabicyclo[2,2,2]octane (i) A mixture of 2-ethyl-2-hydroxymethyl-propan-1,3-diol(13.4 gms) (prepared in an anologous method to 2-n-propyl-2-hydroxymethyl-propan-1,3-diol (Ex. 3(*i*)), diethyl carbonate (12.3 ml), potassium hydroxide (0.1 gm) and dry ethanol (1 ml)was heated to gentle reflux (oil bath 110°–120°) under a stream of nitrogen for 30 minutes. After this time the ethanol formed was removed by distillation at atmospheric pressure (oil bath 130°–140°, still head temperature <76°). The pressure was reduced to 20 mm Hg and the oil bath temperature adjusted to 230°. 3-ethyl-3-hydroxymethyloxetane distilled as a colourless liquid (9.1 g., head temperature 150°).

Gas-liquid chromatography (g.l.c.) : OV-210 at 100° produced one peak. Nuclear magnetic resonance spectrum (N.M.R.) was as follows : $^1$H(ppm from TMS in $CDCl_3$, integral, multiplicity, JHz): 4.40, 4 H, s; 3.70, 2 H, m; 1.7, 2 H, q, 8; 0.9, 3 H, t, 8.

(ii) A solution of 4-iodobenzoyl chloride (11.5 gms) in dry ether (50 ml) was added to a stirred solution of 3-ethyl-3-hydroxymethyloxetane (5 gms) and pyridine (3.5 mls) in ether (100 ml) at 0° C. The resulting mixture was allowed to warm to room temperature and stirred for 24 hours. After this time the mixture was washed with water and brine. The organic extracts were dried over anhydrous magnesium sulphate and then evaporated in vacuo. The residue was purified by column chromatography on silica (preeluted with 1% triethylamine in hexane) and eluted with 5% ethyl acetate in hexane. 3-Ethyl-3-(4-iodobenzoyloxymethyl) oxetane was obtained as a colourless oil (8.1 gms).

Nuclear magnetic resonance spectrum (N.M.R.) was as follows : $^1$H (ppm from TMS in CDCl$_3$, integral, multiplicity JHz): 7.60, 4 H, s; 4.60–4.35, 6 H, m; 1.8, 2 H, q, 8; 0.95, 3 H, q, 8.

(iii) Boron trifluoride etherate (0.44 ml) was added to a stirred solution of 3-ethyl-3-(4-iodobenzoyloxymethyl-oxetane 4.9 gms) in dry dichloromethane (30 ml) at −70° under nitrogen. The resulting mixture was allowed to warm to room temperature and then stirred for 20 hours. After this time triethylamine (2 mls) was added. The reaction mixture was washed with water and the organic layer was dried over anhydrous potassium carbonate and then evaporated in vacuo. The residue was purified by chromatography on alumina, eluting with 40% hexane in dichloromethane saturated with ammonia. 4-Ethyl-1-(4-iodophenyl)-2,6,7-trioxabicyclo[2,2,2]octane was obtained as a white solid (2.9 gms).

Gas-liquid chromatography (g.l.c.) : OV-210 at 230° produced one peak.

Nuclear magnetic resonance spectrum (N.M.R.) was as follows : $^1$H (ppm from TMS in CDCl$_3$, integral, multiplicity, JHz) : 7.60, 2 H, d, 8; 7.30, 2 H, d, 8; 4.05, 6 H, s; 1.5–0.7, 5 H, m.

(iv) Bis-triphenylphosphine palladium dichloride (60 mg) and cuprous iodide (10 mg) were added to a stirred solution of 4-ethyl-1-(4-iodophenyl)-2,6,7-trioxabicyclo[2,2,2]octane (1.5 gms) and trimethylsilylacetylene (0.92 ml) in dry diethylamine (40 ml) under nitrogen. The resulting mixture was stirred at room temperature for 16 hours. After this time the solvent was removed under vacuum and the residue extracted with diethylether. The ethereal solution was washed with water, dried over anhydrous magnesium sulphate and evaporated in vacuo. The residue was purified by column chromatography on alumina, eluting with 30% dichloromethane in hexane saturated with ammonia. 4-Ethyl-1-[4-(2-trimethylsilylethynyl)-phenyl]-2,6,7-trioxabicyclo[2,2,2]octane (1.2 gms) was obtained as an off-white solid (1.2 gms) after recrystallisation from hexane.

Gas liquid chromatography (g.l.c.): OV-210 at 230° produced one peak.

Using the methodology described above starting with the appropriate aryl iodide and trimethylsilylacetylene, the following compounds were prepared:
4-ethyl-1-[4-(2-trimethylsilylethynyl)phenyl]-2,6,7-trioxabicyclo[2,2,2]octane
4-n-propyl-1-[4-(2-trimethylsilylethynyl)phenyl]-2,6,7-trioxabicyclo[2,2,2]octane
4-n-butyl-1-[4-(2-trimethylsilylethynyl)phenyl]-2,6,7-trioxabicyclo[2,2,2]octane
4-t-butyl-1-[4-(2-trimethylsilylethynyl)phenyl]-2,6,7-trioxabicyclo[2,2,2]octane
4-t-butyl-1-[3-(2-trimethylsilylethynyl)phenyl]-2,6,7-trioxabicyclo[2,2,2]octane
4-i-butyl-1-[4-(2-trimethylsilylethynyl)phenyl]-2,6,7-trioxabicyclo[2,2,2]octane
4-n-pentyl-1-[4-(2-trimethylsilylethynyl)phenyl]-2,6,7-trioxabicyclo[2,2,2]octane
1-[3-chloro-4-(2-trimethylsilylethynyl)phenyl]-4-n-propyl-2,6,7-trioxabicyclo[2,2,2]-octane
1-[3-nitro-4-(2-trimethylsilylethynyl)phenyl]-4-n-propyl-2,6,7-trioxabicyclo[2,2,2]-octane
4-phenyl-1-[4-(2-trimethylsilylethynyl)phenyl]-2,6,7-trioxabicyclo[2,2,2]octane
4-cyclohexyl-1-[4-(2-trimethylsilylethynyl)phenyl]-2,6,7-trioxabicyclo[2,2,2]octane The 3-chloro-4-iodobenzoic acid and 3-nitro-4-iodobenzoic acid starting materials were prepared by the method of Hodgson and Beard (*J.Chem.Soc.*, 1927,20).

EXAMPLE 2

Ethyl 3-[4-(4-ethyl-2,6,7-trioxabicyclo[2,2,2]oct-1-yl)phenyl]-prop-2-ynoate.

(i) Tetrabutyl ammonium fluoride solution (3.3 ml,1M in tetrahydroforan) was added to a stirred solution of 4-ethyl-1-[4-(2-trimethylsilylethynyl)phenyl]-2,6,7-trioxabicyclo[2,2,2]octane (0.87 gms) in tetrahydrofuran (15 ml). The mixture was stirred for 30 minutes at room temperature when the solvent was removed under vacuum. The residue was taken up in ether and washed with water and brine. The ethereal solution was dried over anhydrous magnesium sulphate and evaporated in vacuo. Recrystallisation from hexane gave 4-ethyl-1-(4-ethynylphenyl)-2,6,7-trioxabicyclo[2,2,2]octane as an off-white solid (0.66 gms).

Gas-liquid chromatography (g.l.c.): OV-210 at 230° produced one peak.

Nuclear magnetic resonance spectrum (N.M.R.) was as follows : $^1$H (ppm from TMS in CDCl$_3$.integral, multiplicity) : 7.50, 4 H, m; 4.1, 6 H, s; 3.1, 1 H, s; 1.6–0.7, 5 H, m.

(ii) n-Butyl lithium solution (0.67 ml, 1.6M in hexane) was added to a stirred solution of 4-ethyl-1-(4-ethynylphenyl)-2,6,7-trioxabicyclo[2,2,2]octane (200 mg) in tetrahydrofuran (5 ml) at 0° C. under nitrogen. The solution was maintained at 0° C. for 10 minutes when ethyl chloroformate (0.1 ml) was added neat. The solution was allowed to warm to room temperature over 1.5 hours. The reaction was quenched with water (1 ml) and the solvent was removed under vacuum. The residue was taken up in ether and washed with water and brine. The ethereal solution was dried over anhydrous magnesium sulphate and then evaporated in vacuo. The residue was extracted with boiling hexane and afforded ethyl 3-[4-(4-ethyl-2,6,7-trioxabicyclo[2,2,2]oct-1-yl)phenyl]prop-2-ynoate (67 mg) as an off-white crystalline solid on cooling.

Gas-liquid chromatography (g.l.c.) : OV-17 at 230° produced one peak.

Using the methodology described in (i) above, starting from the appropriate trimethylsilylethynyl analogues prepared in example 1, the following compounds were prepared :
4-ethyl-1-(4-ethynylphenyl)-2,6,7-trioxabicyclo[2,2,2]octane
1-(4-ethynylphenyl)-4-n-propyl-2,6,7-trioxabicyclo[2,2,2]octane
4-n-butyl-1-(4-ethynylphenyl)-2,6,7-trioxabicyclo[2,2,2]octane
4-i-butyl-1-(4-ethynylphenyl)-2,6,7-trioxabicyclo[2,2,2]octane
1-(4-ethynylphenyl)-4-n-pentyl-2,6,7-trioxabicyclo[2,2,2]octane
4-(2,2-di-methylpropyl)-1-(4-ethynylphenyl)-2,6,7-trioxabicyclo[2,2,2]octane
1-(3-chloro-4-ethynylphenyl)-4-n-propyl-2,6,7-trioxabicyclo[2,2,2]octane 1-(4-ethynyl-3-nitrophenyl)-4-n-propyl-2,6,7-trioxabicyclo[2,2,2]octane 4-phenyl-1-(4-ethynylphenyl)-2,6,7-trioxabicyclo[2,2,2]octane 4-t-butyl-1-(3-ethynylphenyl)-2,6,7-trioxabicyclo[2,2,2]octane 4-t-butyl-1-(4-ethynylphenyl)-2,6,7-trioxabicyclo[2,2,2]octane Using the methodology described in (ii) above and starting from 1-(4-ethynylphenyl)-4-n-propyl-2,6,7-trioxabicyclo[2,2,2]octane and methyl chloroformate, methyl 3-[4-(4-n-propyl-2,6,7-trioxabicyclo[2,2,2]oct-1-yl)phenyl]prop-2-ynoate was prepared.

The nmr data for these products is provided in the table other than for 4-t-butyl-1-(3-ethynylphenyl)-2,6,7-trioxabicyclo[2,2,2]octane which gave the following NMR spectrum : $^1$H (ppm from TMS in CDCl$_3$, integral, number of peaks): 7.75–7.20,4 H,m; 4.15,6 H,s; 3.0,1 H,s; 0.90,9 H,s.

EXAMPLE 3

1-[4-(3-Methoxyprop-1-ynyl)phenyl]-4-propyl-2,6,7-trioxabicyclo[2,2,2]octane (i) To a stirred mixture of n-valeraldehyde (172 g) and water (2 l.) was added solid calcium hydroxide (112 g.) and formaldehyde solution (1.4 l. of 40% aqueous solution). The reaction temperature was maintained below 40° and the addition took about 45 minutes. The mixture was then maintained at 60° for 5 hours. The reaction mixture was filtered through Kieselguhr and the filtrates were evaporated in vacuo. The residue was treated with hot methanol (2 l.) and the mixture was filtered through Kieselguhr. The filtrates were evaporated in vacuo. A viscous oily product was obtained (458 g.) and was purified as follows:

A solution of the crude product and acetic acid (200 ml.) was stirred at room temperature. Acetic anhydride (1.2 l.) was added over 4 hours. The temperature rose to 65°. Stirring was continued for 12 hours. The reaction mixture was added over 3 hours to cold water (3 l.) with stirring. Stirring was continued for 3 hours. The aqueous mixture was extracted with diethyl ether. The ether extracts were washed with aqueous sodium hydrogen carbonate solution and then with brine. The extracts were dried over anhydrous magnesium sulphate and then evaporated in vacuo.

Distillation gave 2-n-propyl-2-hydroxymethyl-propan-1,3-diol triacetate (238 g.), a colourless oil (b.pt. 120°–140°, 1.5 mm).

Nuclear magnetic resonance spectrum (NMR) was as follows : $^1$H (ppm from TMS in CDCl$_3$, integral, number of peaks): 4.00, 6 H, s; 2.10, 9 H, s; 1.40, 4 H, m; 1.00, 3 H, m.

Sodium (0.5 g.) was added to a stirred solution of the above triacetate (238 g.) in methanol (2.5 l.). The mixture was refluxed, with stirring, for 72 hours. The mixture was evaporated in vacuo.

2-n-Propyl-2-hydroxymethyl-propan-1,3-diol (87 g.) was obtained as colourless crystals (m.pt. 93°).

ref. W. E. Conrad, L. A. Levasseur, R. F. Murphy, N. L. Hare and H. E. Conrad. *J.Org.Chem.* 1962,27,2227.

2-n-Butyl-2-hydroxymethyl-propan-1,3-diol and 2-n-pentyl-2-hydroxymethyl-propan-1,3-diol were prepared from n-hexanal and n-heptanal respectively in a manner analogous to that described for the synthesis of 2-n-propyl-2-hydroxymethyl-propan-1,3-diol.

2-Cyclohexyl-2-hydroxymethylpropan-1,3-diol and 2-isobutyl-2-hydroxymethylpropan-1,3-diol were prepared from diethyl cyclohexylmalonate and diethyl i-butylmalonate respectively in a manner analogous to the synthesis of 2-(2,2-dimethylpropyl)-2-hydroxymethylpropane-1,3-diol (example 5).

2-t-Butyl-2-hydroxymethyl-propan-1,3-diol was prepared as in:
Y. Ozoe and M. Eto,
*Agric.Biol.Chem.*
1982,46,411–8.

(ii) 1-(4-Iodophenyl)-4-propyl-2,6,7-trioxabicyclo[2,2,2]octane was prepared from 2-n-propyl-2-hydroxymethyl-propan-1,3-diol and 4-iodobenzoyl chloride using the method described in Example 1 stages (i)–(iii)

Gas-liquid chromatography (g.l.c.) : OV-210 at 230° produced one peak.

Nuclear magnetic resonance spectrum (N.M.R.) was as follows : $^1$H(ppm from TMS in CDCl$_3$, integral, multiplicity, JHz) : 7.65, 2 H, d, 8; 7.30, 2 H, d, 8; 4.1, 6 H, s; 1.5–0.8, (iii) Bis-triphenylphosphine palladium dichloride (15 mg) and cuprous iodide (5 mg) were added to a stirred solution of 1-(4-iodophenyl)-4-propyl-2,6,7-trioxabicyclo[2,2,2]octane (0.25 gms) and methylpropargyl ether (0.09 ml) in dry diethylamine (5 ml) under nitrogen.

The resulting mixture was stirred at room temperature for 20 hours. After this time the solvent was removed under vacuum and the residue extracted with diethyl ether. The ethereal solution was washed with water, dried over anhydrous magnesium sulphate and evaporated in vacuo. The residue was purified by column chromatography on alumina, eluting with 30% dichloromethane in hexane saturated with ammonia. 1-[4-(3-Methoxyprop-1-ynyl)phenyl]-4-propyl-2,6,7-trioxabicyclo[2,2,2]octane was obtained as an off-white solid (67 mg) after recrystallisation from hexane.

Gas-liquid chromatography (g.l.c.) : OV-17 at 240° produced one peak.

In an analogous manner the following compounds were prepared from 1-(4-iodophenyl)-4-propyl-2,6,7-trioxabicyclo[2,2,2]octane and the respective acetylene components (which are indicated in brackets) :

4-propyl-1-[4-(2-trimethylsilylethynyl)phenyl]-2,6,7-trioxabicyclo[2,2,2]octane.
 (trimethylsilylacetylene).

3-[4-(4-propyl-2,6,7-trioxabicyclo[2,2,2]octyl)phenyl]-prop-2-yn-1-ol.
 (propargyl alcohol).

1-[4-(2-phenylethynyl)phenyl]-4-propyl-2,6,7-trioxabicyclo[2,2,2]octane
 (phenylacetylene).

1,1-dimethyl-3-[4-(4-propyl-2,6,7-trioxabicyclo[2,2,2]oct-1-yl)phenyl]prop-2-yn-1-ol.
 (1,1-dimethylprop-2-yn-1-ol)

4-[4-(4-propyl-2,6,7-trioxabicyclo[2,2,2]octyl)phenyl]-but-3-yn-1-ol.
 (but-3-yn-1-ol)

1-[4-(2-t-butylethynyl)phenyl]-4-propyl-2,6,7-trioxabicyclo[2,2,2]octane
 (3,3-dimethylbut-1-yne))

In an analogous manner the following compounds were prepared from the appropriate 1-(4-iodophenyl)-4-substituted-2,6,7-trioxabicyclo[2,2,2]octane and the respective acetylene component (which is indicated in brackets in each case).

4-t-butyl-1-[4-(3-methoxyprop-1-ynyl)phenyl]-2,6,7-trioxabicyclo[2,2,2]octane (methyl propargyl ether)

1-[3-chloro-4-(3-methoxyprop-1-ynyl)phenyl]-4-n-propyl-2,6,7-trioxabicyclo[2,2,2]octane (methyl propargyl ether)

4-cyclohexyl-1-[4-(3-methoxyprop-1-ynyl)phenyl]-2,6,7-trioxabicyclo[2,2,2]octane (methyl propargyl ether)

1-[4-(3-ethoxyprop-1-ynyl)phenyl]4-n-propyl-2,6,7-trioxabicyclo[2,2,2]octane (ethyl propargyl ether)

4-methoxy-1-[4-(4-n-propyl-2,6,7-trioxabicyclo[2,2,2]oct-1-yl)phenyl]but-1-yne (4-methoxybut-1-yne)

4-i-butyl-1-[4-(3-methoxyprop-1-ynyl)phenyl]-2.6.7-trioxabicyclo[2,2,2]octane (methyl propargyl ether)

N-[3-[4-(4-n-propyl-2,6,7-trioxabicyclo[2,2,2]oct-1-yl)phenyl]prop-2-ynyl]acetamide
(N-prop-2-ynyl acetamide—*Chem.Abs.*, 54: 3178*h*)

4-n-butyl-1-[4-(3-methoxyprop-1-ynyl)phenyl]-2,6,7-trioxabicyclo[2,2,2]octane (methyl propargyl ether)

1-[4-(3-methoxyprop-1-ynyl)phenyl]-4-n-pentyl-2,6,7-trioxabicyclo[2,2,2]octane (methyl propargyl ether)

1-[4-(pent-1-ynyl)phenyl]-4-n-propyl-2,6,7-trioxabicyclo[2,2,2]octane (pent-1-yne)

EXAMPLE 4

1-[4-(3-Methoxyprop-1-ynyl)phenyl]-4-n-propyl-3-trifluoromethyl-2,6,7-trioxabicyclo[2,2,2]octane (i) Sodium hydride (8.0 g 60% dispersion in oil) was added to a stirred solution of diethyl n-propylmalonate (40 g.) in dry benzene (200 ml.). The mixture was maintained at 60°, with stirring, for 1 hour. The mixture was cooled and trifluoracetic anhydride (28 ml.) was added carefully. The mixture was stirred at room temperature for 2 hours. Water was added and the aqueous mixture was extracted with diethyl ether. The ethereal extracts were washed with water, dried over anhydrous magnesium sulphate and evaporated in vacuo.

Distillation gave diethyl 2-n-propyl-2-trifluoroacetylmalonate, a colourless oil (b.pt, 73°, 0.2 m.m.)(35 g.).

Gas-liquid chromatography (g.l.c.) : OV 210 at 130° produced one peak.

Nuclear magnetic resonance spectrum (NMR) was as follows : $^1$H (ppm from TMS in CDCl$_3$, integral, number of peaks, J$_{Hz}$):

4.30, 4 H, q, 8; 2.00, 2 H, m; 1.50–0.70, 11 H, m.

(ii) Lithium aluminium hydride (5.5 g.) in dry diethyl ether (200 ml.) was stirred at 0° under a current of nitrogen. Diethyl 2-n-propyl-2-trifluoroacetyl-malonate (25.0 g.) in dry diethyl ether (50 ml) was added and the mixture was stirred at room temperature for 3 hours. The mixture was then refluxed, with stirring, for 4 hours. The mixture was cooled and a solution of sodium hydroxide (20 g.) and potassium hydrogen phosphate (20 g.) in water (150 ml.) was added carefully. The solid was filtered off and air-dried. The filtrates were evaporated to dryness in vacuo. All the solids were combined and extracted with hot chloroform for 48 hours (soxhlet extraction). The extracts were evaporated in vacuo.

3,3-Di-(hydroxymethyl)-1,1,1-trifluorohexan-2-ol was obtained as a yellow viscous oil (11.0 g.) and was used without further purification.

Infrared spectrum (1 R) liquid film:

3340 (strong and broad), 1155(s), 1100(s), 1040(m), 1020(m).

Nuclear magnetic resonance spectrum (NMR) was as follows : $^1$H (ppm from TMS in CDCl$_3$, integral, number of peaks):

4.20, 1 H, m; 4.00–3.10, 7 H, m; 1.30, 4 H, m; 0.90, 3 H, m.

(iii) A mixture of 3,3-di-(hydroxymethyl)-1,1,1-trifluorohexan-2-ol (2.8 g.), diethyl carbonate (1.6 ml.), potassium hydroxide (0.1 g) and dry ethanol (4.0 mls) was refluxed gently (oil bath 110°), under a current of nitrogen, for 30 minutes. The ethanol was then removed by distillation. Distillation gave 3-(1-hydroxy-2,2,2-trifluoroethyl)-3-n-propyloxetane (1.7 g.), a colourless oil (b.p. 112°, 20–25 m.m).

Gas-liquid chromatography (g.l.c.) : OV 210 at 120° produced one peak.

Infrared spectrum (1 R) (liquid film) :

3450 (s,br), 1300 (s), 1170(s), 1130(s), 1045 (s).

(iv) A solution of 4-iodobenzoyl chloride (2.1 g.) in dry dichloromethane (25 mls) was added to a stirred solution of 3-(1-hydroxy-2,2,2-trifluoroethyl)-3-n-propyl-oxetane (1.55 g.) and pyridine (1.0 ml.) in dry dichloromethane, at 0°. The reaction mixture was stirred for 24 hours, at room temperature. The mixture was poured into water and the aqueous mixture was extracted with diethyl ether. The ethereal extracts were washed with water, dried over anhydrous magnesium sulphate and evaporated in vacuo. The residue was purified by column chromatography on silica, eluting with 1% triethylamine in hexane.

3-[1-(4-Iodobenzoyloxy)-2,2,2-trifluoroethyl]-3-n-propyloxetane was obtained as a colourless oil (2.4 g.).

Gas-liquid chromatography (g.l.c.):OV 210 at 200° produced one peak.

Nuclear magnetic resonance spectrum (NMR) was as follows: $^1$H (ppm from TMS in CDCl$_3$, integral, number of peaks):

7.70, 4H, m; 4.80–4.20, 5H, m; 2.20–0.80, 7H, m.

(v) Boron trifluoride etherate (0.54 ml.) was added to a stirred solution of 3-[1-(4-iodobenzoyloxy)-2,2,2-trifluoroethyl]-3-n-propyloxetane (2.3 g.) in dry dichloromethane (50 mls.) at −70°. The mixture was allowed to warm up slowly to room temperature and was then stirred for 12 hours. Triethylamine (1.0 ml.) was added and the mixture was poured into water. The aqueous mixture was extracted with diethyl ether. The ethereal extracts were washed with water, dried over anhydrous magnesium sulphate and evaporated in vacuo. The residue was purified by column chromatography on alumina eluting with 1:4 dichloromethane:hexane saturated with ammonia.

1-(4-Iodophenyl)-4-n-propyl-3-trifluoromethyl-2,6,7-trioxabicyclo[2,2,2]octane was obtained as a colourless solid (0.53 g.).

Gas-liquid chromatography (g.l.c.) : OV210 at 220° produced one peak.

Nuclear magnetic resonance spectrum (N.M.R.) was as follows: $^1$H (ppm from TMS in CDCl$_3$, integral, number of peaks, J$_{Hz}$):

7.70, 2H, d, 8; 7.30, 2H, d, 8; 4.80–3.80, 5H, m; 1.40, 4H, m;

1.00, 3H, m (vi) 1-[4-(3-Methoxyprop-1-ynl)phenyl[-4-n-propyl-3-trifluoromethyl-2,6,7-trioxabicyclo[2,2,2]octane was prepared from 1-(4-iodophenyl)-4-n-propyl-3-trifluoromethyl-2,6,7-trioxabicyclo[2,2,2]octane and methyl propargyl ether using the methodology described in Example 3.

4-n-Butyl-1-[4-(3-methoxyprop-1-ynyl)phenyl]-3-trifluoromethyl-2,6,7-trioxabicyclo[2,2,2]octane was prepared from diethyl n-butyl-malonate in a manner analogous to the synthesis of 1-[4-(3-methoxyprop-1-ynyl)- phenyl]-4-n-propyl-3-trifluoromethyl-2,6,7-trioxabicyclo[2,2,2]octane

EXAMPLE 5

4-(2,2-Dimethylpropyl)-1-[4-(3-methoxyprop-1-yl)phenyl]-2,6,7-trioxabicyclo[2,2,2]octane (i) Diethyl 2,2-dimethylpropylmalonate (18.8 g.) (Brandstrom, *Acta. Chem. Scand.*, 1958, 13, 615) was added to a stirred suspension of sodium hydride (4.0 g., 60% dispersion in oil) in dry tetrahydrofuran (150 ml.), at 0°, under nitrogen. The mixture was refluxed, with stirring, for one hour. The mixture was cooled and benzyl chloromethyl ether (13.3 g.) in dry tetrahydrofuran (50 ml.) was added dropwise. The reaction mixture was stirred for 24 hours and poured into cold water. The aqueous mixture was extracted with diethyl ether. The ethereal extracts were washed with water and dried over anhydrous magnesium sulphate. The solvent was removed in vacuo.

Diethyl 2-benzyloxymethyl-2-(2,2-dimethyl-propyl) malonate was obtained as an oil (28.8 g.) and was used without further purification.

(ii) Diethyl 2-benzyloxymethyl-2-(2,2-dimethylpropyl)malonate (15 g.) in dry diethyl ether (50 ml.) was added slowly to a stirred suspension of lithium aluminium hydride (7.0 g.) in dry diethyl ether (200 ml.) at 0°, under nitrogen. The mixture was stirred at room temperature for 12 hours. Aqueous sodium hydroxide solution (25 ml., 10% solution) was added carefully. The mixture was filtered and the solid was washed with diethyl ether. The filtrates were dried over anhydrous magnesium sulphate and evaporated in vacuo. The residue was purified by chromatography on silica, eluting with 1:4 ethyl acetate:hexane. 2-Benzyloxymethyl-2-(2,2-dimethylpropyl)-propan-1,3-diol was obtained as a colourless oil (5.5 g.).

(iii) 2-Benzyloxymethyl-2-(2,2-dimethylpropyl)-propan-1,3-diol (5.5 g.) in dry diethyl ether (50 ml.) was added to liquid ammonia (200 ml.) at −70°. Sodium (2.5 g.) was added to the stirred solution. Stirring was maintained at −70°, for 1 hour. The mixture was allowed to warm up to −30° and solid ammonium chloride (15 g.) was added cautiously. The ammonia was removed from the reaction mixture under a current of nitrogen. Methanol (25 ml.) was added to the stirred mixture to destroy residual sodium. Dichloromethane (400 ml.) was added and the mixture was filtered. The filtrates were evaporated in vacuo. 2-(2,2-Dimethylpropyl)-2-hydroxymethyl-propan-1,3-diol was obtained as a colourless solid (3.5 g.).

Nuclear magnetic resonance spectrum (NMR) was as follows: $^1$H (p.p.m.

from TMS in CDCl$_3$, integral, number of peaks):

4.20, 3H, broad, exchanged with D$_2$O; 3.80, 6H, s; 1.40, 2H, s; 1.20, 9H, s.

(iv) Trimethyl 4-bromo-orthobenzoate (1.5 g.) (McElvain and Venerable, *J. Amer.Chem.Soc.*, 1950,72,1661) was added to 2-(2,2-dimethylpropyl)-2-hydroxymethyl-propan-1,3-diol (1.0 g.). One drop of concentrated hydrochloric acid was added and the mixture was maintained at 140° for one hour, under a current of nitrogen. The volatile components were removed in vacuo (1.0 mm), at 140° C.

The residue was purified by chromatography on alumina (Alumina Woelm TSC), eluting with 1:20 dichloromethane:hexane, saturated with ammonia. 1-(4-Bromophenyl)-4-(2,2-dimethylpropyl)-2,6,7-trioxabicyclo[2,2,2]octane was obtained as a colourless solid (0.70 g.).

Gas-liquid chromatography (g.l.c.):
OV101 at 250° produced one peak.

Nuclear magnetic resonance spectrum (NMR) was as follows: $^1$H (ppm from TMS in CDCl$_3$.integral, number of peaks):

7.50, 4H, s; 4.20, 6H, s; 1.20, 2H, s; 1.00, 9H, s.

Mass Spectrum (M.S.), Chemical Ionisation:
M+1,341,343.

(v) n-Butyllithium (5.0 ml.of 1.6 M solution in hexane) was added to a stirred solution of 1-(4-bromophenyl)-4-(2,2-dimethylpropyl)-2,6,7-trioxabicyclo[2,2,2]octane (0.5 g.) in dry diethyl ether (50 ml) at −70°, under a current of nitrogen. The reaction mixture was allowed to warm up slowly to room temperature and the progress of the reaction was monitored by gas liquid chromatographic analysis. When all the starting material had disappeared iodine (1.0 g.) in dry diethyl ether (50 ml.) was added to the stirred reaction mixture. After 10 minutes on aqueous solution of sodium thiosulphate (3 g. in 40 ml. water) was added. The aqueous mixture was extracted with diethyl ether. The ethereal extracts were washed with water, dried over anhydrous magnesium sulphate and evaporated in vacuo. The residue was purified by chromatography on alumina, eluting with 5% dichloromethane:hexane, saturated with ammonia.

4-(2,2-Dimethylpropyl)-1-(4-iodophenyl)-2,6,7-trioxabicyclo[2,2,2]octane was obtained as a colourless solid.

Nuclear magnetic resonance spectrum (NMR) was as follows: $^1$H (ppm from TMS in CDCl$_3$, integral, number of peaks):

7.70, 2H, d, 7; 7.35, 2H, d, 7; 4.20, 6H, s; 1.30, 2H, s; 1.00, 9H, s.

Mass Spectrum (M.S.), Chemical Ionisation:
M+1,389.

(vi) Using methodology described in Example 3, 4-(2,2-dimethylpropyl)-1-[4-(3-methoxyprop-1-ynyl)-phenyl]-2,6,7-trioxabicyclo [2,2,2] octane was prepared from 4-(2,2-Dimethylpropyl)-1-(4-iodophenyl)-2,6,7-trioxabicyclo-[2,2,2]octane and methyl propargyl ether.

(vii) Using methodology described in Example 1, 4-(2,2-dimethylpropyl)-1-[4-(2-trimethylsilylethynyl)-phenyl]-2,6,7-trioxabicyclo[2,2,2]octane was prepared from 4-(2,2-dimethyl-propyl)-1-(4-iodophenyl)-2,6,7-trioxabicyclo[2.2.2]octane and trimethylsilylacetylene.

EXAMPLE 6

N-Methyl-3-[4-(4-n-propyl-2,6,7-trioxabicyclo[2,2,2]oct-1-yl)phenyl]prop-2-ynyl carbamate A solution of 3-[4-(4-n-propyl-2,6,7-trioxabicyclo[2,2,2]octyl)phenyl]-prop-2-yn-1-ol (0.5 g), methyl isocyanate (0.2 g), and triethylamine (0.1 g) in dry benzene (50 ml) was refluxed for 6 hours. The solution was cooled and evaporated in vacuo.

The residue was purified by chromatography on alumina, eluting with 1:5 dichloromethane: hexane, saturated with ammonia.

N-Methyl-3-[4-(4-n-propyl-2,6,7-trioxabicyclo[2,2,2]oct-1-yl) phenyl] prop-2-ynyl carbamate was obtained as a colourless solid (0.25 g m.p.t. 136.2°).

EXAMPLE 7

3-[4-(4-n-Propyl-2,6,7-trioxabicyclo[2,2,2]oct-1-yl)phenyl]prop-2-ynyl acetate Acetyl chloride (0.33 ml) was added to a stirred solution of 3-[4-(4-n-propyl-2,6,7-trioxabicyclo[2,2,2]octyl)- phenyl]-prop-2-yn-1-ol (1.1 g) and triethylamine (0.8 ml) in dry diethyl ether, at 0° C., under nitrogen. The mixture was stirred for 12 hours at room temperature and poured into water. The aqueous mixture was extracted with diethyl ether. The ethereal extracts were washed with water, dried over anhydrous magnesium sulphate and evaporated in vacuo.

The residue was purified by chromatography on alumina, eluting with 3:2 dichloromethane:hexane, saturated with ammonia.

3-[4-(4-n-Propyl-2,6,7-trioxabicyclo[2,2,2]oct-1-yl)phenyl]prop-2-ynyl acetate was obtained as colourless crystals (0.90 g m.p.t. 98.0°).

N,N-Dimethyl-3-[4-(4-n-propyl-2,6,7-trioxabicyclo[2,2,2]oct-1-yl)phenyl]-prop-2-ynamide and N,N-dimethyl-3-[4-(4-n-propyl-2,6,7-trioxabicyclo[2,2,2]oct-1-yl)phenyl]-prop-2-ynthioamide were prepared using similar methodology from 1-(4-ethynylphenyl)-4-n-propyl-2,6,7-trioxabicyclo[2,2,2]ootane and dimethylcarbamoyl chloride and dimethylthiocarbamoyl chloride respectively.

EXAMPLE 8

4-n-Propyl-1-[4-(prop-1-ynyl)-phenyl]-2,6,7-trioxabicyclo[2,2,2]octane n-Butyllithium (0.79 ml of 1.6M solution, in hexane) was added to a stirred solution of 1-(4-ethynylphenyl)-4-n-propyl-2,6,7-trioxabicyclo[2,2,2]octane (0.25 g) in dry tetrahydrofuran, at 0°, under nitrogen. The reaction was stirred at 0° for 10 minutes. Methyl iodide (90 μl) was added and the mixture was stirred at room temperature for 5 hours. The solvent was removed in vacuo.

Water was added and the aqueous mixture was extracted with diethyl ether. The ethereal extracts were washed with water, dried over anhydrous magnesium sulphate and evaporated in vacuo.

4-n-Propyl-1-[4-(prop-1-ynyl)-phenyl]-2,6,7-trioxabicyclo[2,2,2]octane was obtained as colourless crystals (0.20 g., recrystallised from dichloromethane:hexane).

EXAMPLE 9

3-Cyano-1-[4-(3-methoxyprop-1-ynyl)phenyl]-4-n-propyl-2,6,7-trioxabicyclo [2,2,2] octane (i) A mixture of 2-n-propyl-2-hydroxymethyl-propan-1,3-diol (24.6 g), diethyl carbonate (20.1 ml.), potassium hydroxide (0.3 g) and dry ethanol (2 ml) was heated to gentle reflux (oil bath 110–120°) under a stream of nitrogen for 30 minutes. After this time the ethanol formed was removed by distillation at atmospheric pressure (oil bath 130–140°, still head temperature 76°). The pressure was reduced to 20 mm.Hg and the oil bath temperature adjusted to 230°. 3-hydroxymethyl-3-n-propyl oxetane distilled as a colourless liquid (16.7 gms, head temperature 120–126°).

Gas-liquid chromatography (g.l.c.): OV-210 at 120° produced one peak. Nuclear magnetic resonance spectrum (N.M.R.) was as follows: $^1$H (ppm from TMS in CDCl$_3$, integral, multiplicity): 4.35, 4H, s; 3.60, 2H, m; 1.8–0.7, 7H, m.

(ii) A solution of dimethyl sulphoxide (12 ml) in dry dichloromethane (4.0 ml) was added to a solution of oxalyl chloride (7.4 ml) in dichloromethane (25 ml) stirred at −70° under nitrogen. After the addition was complete the resulting mixture was stirred for a futher 5 minutes at −70° before a solution of 3-hydroxymethyl-3-n-propyloxetane (10.0 g) in dichloromethane (25 ml) was added, dropwise, over 10 minutes. The resulting mixture was allowed to stir for a further 30 minutes when neat triethylamine (54 ml) was added over approximately 30 minutes. The reaction mixture was allowed to warm to room temperature over 3 hours when it was poured into water. The organic phase was separated and the aqueous layer further extracted with fresh dichloromethane. The combined organic extracts were washed with dilute hydrochloric acid, saturated sodium bicarbonate and brine. The resulting organic phase was dried over anhydrous magnesium sulphate and evaporated in vacuo to give 3-formyl-3-n-propyloxetane (10.5 g) as a yellow oil.

Gas-liquid chromatography (g.l.c.):OV-210 at 120° produced one peak.

Infrared spectrum (1R) (liquid film):1730 cm $^{-1}$.

Nuclear magnetic resonance spectrum (N.M.R]) was as follows: $^1$H (ppm from TMS in CDCl$_3$, integral, multiplicity, JH$_z$; 9.0, 1H, s; 4.90, 2H, d, 6; 4.60, 2H, d, 6; 2.30–1.0, 7H, m.

(iii) To a stirred solution of 3-formyl-3-n-propyl-oxetane (3.0 g) and 4-iodobenzoyl chloride (6.2 g) in diethyl ether (75 ml), under nitrogen, was added a solution of sodium cyanide (1.6 g) in water (2.0 ml). The mixture was stirred overnight. The mixture was poured into water (50 ml) and the aqueous mixture was extracted diethyl ether. The ethereal solution was dried over anhydrous sodium sulphate and then evaporated in vacuo. The residue was chromatographed on silica pre-treated with triethylamine and eluting with hexane:chloroform 1:3.

The 4-iodobenzoate of 3-(α-cyano-hydroxymethyl)-3-n-propyl-oxetane was obtained as a colourless solid (6.5 g m.p.t. 90°).

Nuclear magnetic resonance spectrum (NMR) was as follows: $^1$H (ppm from TMS in CDCl$_3$, integral, number of peaks, JH$_z$):

7.90, 2H, d, 7; 7.80, 2H, d, 7; 5.70, 1H, s; 4.65, 4H, m; 1.95, 2H, m;

1.50, 2H, m; 1.00, 3H, t, 6.

Mass Spectrum (M.S.), Chemical Ionisation: M+1, 386.

(iv) Using methodology described in stage iii of Example 1, 3-cyano-1-(4-iodophenyl)-4-n-propyl-2,6,7-trioxabicyclo [2,2,2] octane (colourless, crystals, mpt 129°) was prepared from the 4-iodobenzoate of 3-(α-cyano-hydroxymethyl)-3-n-propyl-oxetane.

Nuclear magnetic resonance spectrum (NMR) was as follows: $^1$H (ppm from TMS in CDCl$_3$, integral, number of peaks, JH$_z$):

7.75, 2H, d, 7; 7.35, 2H, d, 7; 4.95, 1H,d, 2; 4.40, 1H, m; 4.15, 3H, m;

1.60–1.40, 4H, m; 1.00, 3H, t, 6.

Mass Spectrum (MS), Chemical Ionisation: M+1, 386.

(v) Using methodology described in Example 3, 3-cyano-1-[4-(3-methoxyprop-1-ynyl)phenyl]-4-n-propyl-2,6,7-trioxabicyclo[2,2,2]octane was prepared from 3-cyano-1-(4-iodophenyl)-4-n-propyl-2,6,7-trioxabicyclo[2,2,2]-octane.

EXAMPLE 10

1-[4-(3-Methoxyprop-1-ynyl)-phenyl]-4-n-propyl-2,6-dioxa-7-thiabicyclo[2,2,2]-octane (i) Diethyl n-propyl malonate (20.0 g) was added to a stirred suspension of sodium hydride (4.8 g. 50% dispersion in oil) in dry toluene (200 ml.), under nitrogen. The mixture was stirred at 80° for one hour. The mixture was cooled and benzyl chloromethyl thioether (J.L. Wood and V.du Vigneaud, J.Biol.Chem.1939,131,267) (16.0 g.) in dry toluene (50 ml) was added and the mixture was stirred at 80° for two hours. The mixture was cooled and poured into water. The aqueous mixture was extracted into diethyl ether. The ether extracts were washed with water, dried over anhydrous magnesium sulphate and evaporated in vacuo. Diethyl 2-benzylthiomethyl-2-n-propyl malonate (30.0 g.) was obtained as a yellow oil and was used without further purification.

(ii) Diethyl 2-benzylthiomethyl-2-n-propyl malonate (30.0 g.) in dry diethyl ether (60 ml.) was added to a stirred suspension of lithium aluminium hydride (7.0 g.) in dry diethyl ether (400 ml.), at 0°, under nitrogen. The mixture was stirred at room temperature for three hours and then refluxed with stirring for a further three hours. The mixture was cooled and 10% aqueous sodium hydroxide solution (25 ml.) was added very carefully. The mixture was filtered and the solid was washed with ether. The filtrates were dried over anhydrous magnesium sulphate and evaporated in vacuo. 2-Benzylthiomethyl-2-n-propyl-propan-1,3-diol was obtained as a colourless solid (20 g.) and was used without further purification.

(iii) 2-Benzylthiomethyl-2-n-propyl-propan-1,3-diol (7.0 g.) in dry diethyl ether (150 ml.) was added to liquid ammonia (150 ml.) at −70°. Sodium (1.8 g.) was added to the stirred solution. Stirring was maintained at −70°, for one hour. The mixture was then allowed to warm up to −30° and solid ammonium chloride (10 g.) was added cautiously.

The ammonia was removed from the reaction mixture under a current of nitrogen. The residue was washed with dry dichloromethane and the filtrates were evaporated in vacuo. 2,2-Di-hydroxymethyl-pentan-1-thiol (3.2 g.) was obtained as a colourless smelly oil and was used without further purification.

(iv) Using a method analogous to that described in stage iv of Example 5 2,2-di-hydroxymethyl-pentan-1-thiol and trimethyl 4-bromo-orthobenzoate were reacted together to give 1-(4-bromophenyl)-4-n-propyl-2,6-dioxa-7-thiabicyclo[2,2,2]octane (colourless solid).

Gas-liquid chromatography (glc): OV 210 at 200° produced one peak.

Nuclear magnetic resonance spectrum (NMR) was as follows: $^1$H (ppm
from TMS in CDCl$_3$, integral, number of peaks):
7.50,4H,s; 4.20, 4H,m; 3.20, 2H,m; 1.40,4H,m; 1.00,3H,m.

Infrared spectrum (1R)(nujol mull): 1080(s),1040(s),1020(m).

Mass spectrum (MS), chemical ionisation:
M+1,329,331.

(v) n-Butyllithium (16 ml., 1.6M solution in hexane) was added to a stirred solution of 1-(4-bromophenyl)-4-n-propyl-2,6-dioxa-7-thiabicyclo[2.2.2]octane (1.7 g) in dry diethyl ether (150 ml) at −70°, under nitrogen. The reaction mixture was allowed to warm up slowly to room temperature and the progress of reaction was monitored by g.l.c. analysis. When all the starting material had disappeared iodine (6.6 g) in dry diethyl ether (50 ml) was added and this was followed immediately by the addition of an aqueous solution of sodium thiosulphate (10 g in 70 ml water). The mixture was extracted with ethyl acetate. The organic layer was washed with water and dried over anhydrous magnesium sulphate. The solvent was removed in vacuo.

The residue was purified by chromatography on alumina (Alumina Woelm TSC) eluting with 1:10 dichloromethane:hexane, saturated with ammonia.

1-(4-Iodophenyl)-4-n-propyl-2,6-dioxa-7-thiabicyclo[2,2,2]octane was obtained as colourless crystals (0.8 g mpt 128–132°)

Nuclear magnetic resonance spectrum (NMR) was as follows: $^1$H (ppm from TMS in CDCl$_3$, integral, number of peaks, JH$_z$); 7.70, 2H, d, 7; 7.40, 2H, d, 7; 4.15, 4H, m;3.10, 2H, m; 1.30, 4H, m; 0.95, 3H, m.

Mass spectrum (MS), chemical ionisation:
M+1, 377.

(vi) A mixture of 1-(4-iodophenyl)-4-n-propyl-2,6-dioxa-7-thiabicyclo[2,2,2]-octane (0.20 g), methyl propargyl ether (67μl) bis(triphenylphosphine)palladium (II) chloride (50 mg) and cuprous iodide (25 g) in dry triethylamine (10 ml) was stirred at room temperature, under nitrogen for 24 hours.

The solvent was removed in vacuo. The residue was extracted with diethyl ether and the ethereal extracts were washed with water. The extracts were dried over anhydrous magnesium sulphate and the solvent was removed in vacuo.

The residue was purified by chromatography on alumina (alumina Woelm TSC), eluting with 1:5 dichloromethane:hexane, saturated with ammonia.

1-[4-(3-Methoxyprop-1-ynyl)phenyl] 4-n-propyl-2,6-dioxa-7-thiabicyclo-[2,2,2]octane was obtained as a colourless solid (20 mg).

Nuclear magnetic resonance spectrum (NMR) was as follows: $^1$H (ppm
from TMS in CDCl$_3$, integral, number of peaks, JH$_z$);
7.60, 2H, d, 6; 7.45, 2H, d, 6; 4.30, 2H, s; 4.20, 4H, m; 3.50, 3H, s; 3.10, 2H, m; 1.30, 4H, m; 0.95, 3H, m.

Mass spectrum (MS), chemical ionisation:
M+1, 319.

Using the methodology outlined above 4-n-propyl-1-[4-(2-trimethylsilylethynyl)phenyl]-2,6,-dioxa-7-thiabicyclo[2,2,2]octane was prepared from 1-(4-iodophenyl)-4-n-propyl-2,6-dioxa-7-thiabicyclo[2,2,2]octane and trimethylsilylacetylene and using diethylamine instead of triethylamine as solvent.

4-n-propyl-1-[4-(2-trimethylsilylethynyl)phenyl]2,6-dioxa-7-thiabicyclo[2,2,2]octane was obtained as a colourless crystalline solid.

Nuclear magnetic resonance spectrum (NMR) was as follows: $^1$H (ppm from TMS
in CDCl$_3$, integral, number of peaks, J$_{Hz}$);
7.50,4H,m;4.20,4H,m; 3.15,2H,m; 1.35,4H,m; 1.05,3H,m; 0.40,9H,m.

Mass spectrum (MS), chemical ionisation:
M+1, 347.

1-(4-Ethynylphenyl)-4-n-propyl-2,6-dioxa-7-thiabicyclo[2,2,2]octane was prepared from 4-n-propyl-1-[4-(2-trimethylsilylethynyl)phenyl]-2,6-dioxa-7-thiabicyclo[2,2,2]octane using methodology outlined in stage (i) of Example 2.

1-(4-Ethynylphenyl)-4-n-propyl-2,6-dioxa-7-thiabicyclo[2,2,2]octane was obtained as a colourless solid.

Nuclear magnetic resonance spectrum (NMR) was as follows:$^1$H (ppm from TMS in CDCl$_3$, integral, number of peaks, J$_{Hz}$):
7.50,4H,m; 4.20,4H,m; 3.20,3H,m; 1.30,4H,m; 1.00,3H,m.

Mass spectrum (MS), chemical ionisation:
M+1, 275.

EXAMPLE 11

4-t-Butyl-1-(4-ethynylphenyl)-2,6,7-trioxabicyclo[2,2,-2]octane (i) To a solution of p-vinylbenzoic acid (5 g, 34 mmol) in chloroform (50 ml) at 0° C. was added $Br_2$ (35 mmol) in chloroform with stirring. The mixture was allowed to stand overnight and then was evaporated to dryness, leaving crude 4-(1,2-dibromoethyl)benzoic acid, 10.4 g, (99%). This was suspended in dry benzene (100 ml), thionyl chloride (8.3) was added and the mixture was heated sufficiently to cause it to reflux for 3 hours. The solution was evaporated to dryness to give the acid chloride as a solid.

(ii) To a stirred solution to 3-t-butyl-3-hydroxymethyloxetane (2.16 g, 15 mmol) in dry dichloromethane (30 ml) containing pyridine (1.5 ml) at 0° C. under a nitrogen atmosphere was added a solution of 4-(1,2-dibromoethylbenzoyl chloride (5 g, 16 mmol) from above. The mixture was allowed to warm to room temperature and was stirred overnight. The resulting solution was washed with water, dried over sodium sulfate and evaporated to leave the oxetane ester, 6.5 g. The product was characterised by NMR (300 MHz, $CDCl_3$):δ 1.05, 9H, s; 3.95–4.1, 2H, m; 4.45, 2H, s; 4.6, 4H, d of d; 5.15 1H, d of d; 7.5, 2H, d; 8.1, 2H, d;

To a stirred solution of the oxetane ester (6.5 g, 15 mmol) in dry dichloromethane (35 ml) under a nitrogen atmosphere at −70° C. was added boron trifluoride etherate (1 ml). The solution was allowed to warm to room temperature and was stirred overnight. The reaction mixture was quenched with dry triethylamine and evaporated to dryness. The residue was partitioned between water and dichloromethane and the organic layer was separated, dried over $K_2CO_3$ and evaporated to leave crude 4-t-butyl-1-[4-(1,2-dibromoethyl)-phenyl]-2,6,7-trioxabicyclo[2,2,2]octane. This compound was characterized by NMR (300 MHz, $CDCl_3$); δ 0.9, 9H, s; 3.9–4.05, 2H, m; 4.15, 6H, s; 5.1, 1H, d of d; 7.35, 2H, d; 7.6, 2H, d.

Small pieces of sodium were added to liquid ammonia until a blue colour persisted. Ferric nitrate (100 mg) was added and the solution was stirred. When the solution turned colourless, sodium (6 g) was added in small pieces. After about 30 to 35 minutes following the addition the blue colour disappeared and a solution of the above dibromoethylphenyl bicyclooctane in tetrahydrofuran was added to the solution. The ammonia was allowed to evaporate overnight and the residue was partitioned between ether and ice/water. The organic layer was separated, dried over $K_2CO_3$ and evaporated to leave crude 4-t-butyl-1-(4-ethynylphenyl)-2,6,7-bicyclo[2,2,2]octane. This was purified by chromatography on alumina (made basic with $NH_3$) and elution with dichloromethane-hexane (1:4) and recrystallization from hexane-dichloromethane.

Utilizing the procedure described above (i) 4-cyclohexyl-1-(4-ethynylphenyl)-2,6,7-trioxabicyclo[2,2,2]octane and (ii) 4-n-propyl-1-(4-ethynylphenyl)-2,6,7-trioxabicyclo[2,2,2]octane were prepared from the respective oxetanes.

Thus 3-cyclohexyl-3-hydroxymethyloxetane and 3-n-propyl-3-hydroxymethyloxetane were reacted with 4-(1,2-dibromoethyl)benzoyl chloride by the method of example 11. The resulting products were characterized by NMR (300 MHz, $CDCl_3$).

The oxetane esters so produced were reacted with boron trifluoride etherate as described above to yield (i) 4-cyclohexyl-1-(4-(1,2-dibromoethyl)phenyl)-2,6,7-trioxabicyclo[2,2,2]octane and (ii) 4-n-propyl-1-(4-(1,2-dibromoethyl)phenyl)-2,6,7-trioxabicyclo[2,2,2]octane. The products were characterized by NMR (300 MHz,$CDCl_3$); (i) δ 0.9–1.3 and 1.5–1.9, 11H, m; 3.9–4.1, 2H, m; 4.1 6H,s; 5.1 1H, d of d; 7.35 2H, d; 7.6, 2H, d; (ii) δ0.9, 3H, t, 1.15–1.35, 4H, m, 3.9–4.1, 2H, m; 4.1, 6H, s; 5.1, 1H, d of d; 7.35, 2H,d, aromatic; 7.6, 2H, d;

The dibromoethylphenyl bicyclics were dehydrobrominated as described above to yield the desired 1-(4-ethynylphenyl)-2,6,7-trioxabicyclo[2,2,2]octanes.

EXAMPLE 12

1-[4-(2-t-Butyldimethylsilylethynyl)phenyl]-4-n-propyl-2,6,7-trioxabicyclo[2,2,2]-octane n-Butyllithium (0.79 ml of 1.6M solution, in hexane) was added to a stirred solution of 1-(4-ethynylphenyl)-4-n-propyl-2,6,7-trioxabicyclo[2,2,2]octane (0.25 g.) in dry tetrahydrofuran (15 ml) at 0°, under nitrogen. The reaction mixture was stirred at 0° for 10 minutes. t-Butyldimethylsilyl chloride (0.23 g.) was added and the mixture was stirred at room temperature for 6 hours. The reaction mixture was evaporated in vacuo. Water was added and the aqueous mixture was extracted with diethyl ether. The ethereal extracts were washed with water, dried over anhydrous magnesium sulphate and evaporated in vacuo. The residue was purified by chromatography on alumina (Alumina Woelm TSC), eluting with 2:3 dichloromethane : hexane saturated with ammonia. 1-[4-(2-t-Butyldimethylsilylethynyl)phenyl]-4-n-propyl-2,6,7-trioxabicyclo[2,2,2]octane was obtained as pale yellow crystals (0.32 g.)

Using the above methodology 1-[4-(2-methylthioethynyl)phenyl]-4-n-propyl-2,6,7-trioxabicyclo[2,2,2]octane was prepared from 1-(4-ethynylphenyl)-4-n-propyl-2,6,7-trioxabicyclo[2,2,2]octane and s-methyl methanethiosulphonate (Fluka A.G.).

EXAMPLE 13

N-Methyl-3-[4-(4-n-propyl-2,6,7-trioxabicyclo[2,2,-2]oct-1-yl)phenyl]-prop-2-yn-amide n-Butyllithium (1.6 ml) of 1.6M solution in hexane) was added to a stirred solution of 1-(4-ethynylphenyl)-4-n-propyl-2,6,7-trioxabicyclo[2,2,2]octane (0.5 g) in dry tetrahydrofuran (15 ml), under nitrogen, at 0°. The mixture was stirred at 0° for 10 minutes and methyl isocyanate (0.17 ml.) was added. After 1 hour the mixture was evaporated in vacuo. Water was added and the aqueous mixture was extracted with diethyl ether. The ether extracts were washed with water, dried over anhydrous magnesium sulphate and evaporated in vacuo.

The residue was purified by chromatography on alumina (Alumina Woelm TSC), eluting with 1:4 dichloromethane : hexane saturated with ammonia.

N-Methyl-3-[4-(4-n-propyl-2,6,7-trioxabicyclo[2,2,-2]oct-1-yl)phenyl]-prop-2-ynamide was obtained as colourless crystals (0.095 g.).

N-Methyl-3-[4-(4-n-propyl-2,6,7-trioxabicyclo[2,2,-2]oct-1-yl)phenyl]-prop-2-yn-thioamide was prepared from 1-(4-ethynylphenyl)-4-n-propyl-2,6,7-trioxabicyclo[2,2,2]octane and methyl isothiocyanate in a manner analogous to the synthesis of N-Methyl-3-[4-(4-n-propyl-2,6,7-trioxabicyclo[2,2,2]oct-1-yl)phenyl]-prop-2-ynamide.

EXAMPLE 14

3-[4-(4-n-Propyl-2,6,7-trioxabicyclo[2,2,2]oct-1-yl)phenyl]prop-2-ynyl methanesulphonate Methanesulphonyl chloride (0.19 ml.) was added to a stirred solution of 3-[4-(4-n-propyl-2,6,7-trioxabicyclo[2,2,2]oct-1-yl)phenyl]-prop-2-yn-1-ol (0.6 g.) in dry pyridine (0.34 ml.) and dry dichloromethane (20 ml.) at 0°, under nitrogen. The mixture was stirred for 1 hour at 0°. The mixture was poured into water. The aqueous mixture was extracted with diethyl ether. The ether extracts were washed with water, dried over anhydrous magnesium sulphate and evaporated in vacuo.

The residue was purified by chromatography on alumina (Alumina Woelm TSC) eluting with 1:1 dichloromethane : hexane saturated with ammonia.

3-[4-(4-n-Propyl-2,6,7-trioxabicyclo[2,2,2]oct-1-yl)phenyl]prop-2-ynyl methanesulphonate was obtained as colourless crystals (0.18 g.).

EXAMPLE 15

1-[4-(3-Ethylthioprop-1-ynyl)phenyl]-4-n-propyl-2,6,7-trioxabicyclo[2,2,2]octane To a solution of ethanethiol (0.053 ml.) in dry tetrahydrofuran (20 ml.) at 0°, under nitrogen, was added n-butyllithium (0.45 ml. of 1.6M solution in hexane). The solution was stirred for 10 minutes and a solution of 3-[4-(4-n-propyl-2,6,7-trioxabicyclo[2,2,2]oct-1-yl)phenyl]prop-2-ynyl methanesulphonate (0.25 g.) in dry tetrahydrofuran (5 ml.) was added dropwise. After 2 hours the mixture was evaporated in vacuo. Water was added and the aqueous mixture was extracted with diethyl ether. The ether extracts were washed with water, dried over anhydrous megnesium sulphate and evaporated in vacuo.

The residue was purified by chromatography on alumina (Alumina Woelm TSC), eluting with 1:1 dichloromethane : hexane saturated with ammonia.

1-[4-(3-Ethylthioprop-1-ynyl)phenyl]-4-n-propyl-2,6,7-trioxabicyclo[2,2,2]octane was obtained as an off-white waxy solid (0.21 g.).

EXAMPLE 16

1-[4-(3-Ethylsulphinylprop-1-ynyl)phenyl]-4-n-propyl-2,6,7-trioxabicyclo[2,2,2]octane A solution of 1-[4-(3-ethylthioprop-1-ynyl)phenyl]-4-n-propyl-2,6,7-trioxabicyclo[2,2,2]octane (0.20 g.) and 3-chloroperoxybenzoic acid (0.16 g.) in dichloromethane (25 ml.) was stirred at room temperature for 30 minutes. The solution was washed successively with saturated aqueous sodium hydrogen carbonate solution, water and finally brine. The dichloromethane solution was dried over anhydrous magnesium sulphate and then evaporated in vacuo.

The residue was purified by chromatography on alumina (Alumina Woelm TSC) eluting with 1:1 dichloromethane : hexane saturated with ammonia.

1-[4-(3-Ethylsulphinylprop-1-ynyl)phenyl]-4-n-propyl-2,6,7-trioxabicyclo]2,2,2]octane was obtained as an off-white solid (0.08 g.).

1-[4-(2-Methylsulphinylethynyl)phenyl]-4-n-propyl-2,6,7-trioxabicyclo[2,2,2]octane was prepared by the above method from 1-[4-(2-methylthioethynyl)phenyl[-4-n-propyl-2,6,7-trioxabicyclo[2,2,2]octane.

The various spectra and nuclear magnetic resonance spectra of various compounds of the invention are set in the Table below.

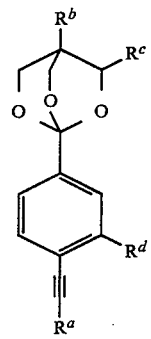

| Compound Number | $R^b$ | $R^a$ | $R^c$ | $R^d$ | M.pt | Mass Spectrum Chemical Ionisation M + 1 | Example |
|---|---|---|---|---|---|---|---|
| 1 | Et | CO$_2$Et | H | H | Solid | 317 | 2 |
| 2 | nPr | CH$_2$OMe | H | H | Solid | 303 | 3 |
| 3 | nPr | CH$_2$OH | H | H | Solid | 289 | 3 |
| 4 | nPr | Phenyl | H | H | Solid | 335 | 3 |
| 5 | nPr | t-butyl | H | H | Solid | 315 | 3 |
| 6 | nPr | C(CH$_3$)$_2$OH | H | H | Solid | 317 | 3 |
| 7 | nPr | CH$_2$CH$_2$OH | H | H | Solid | 303 | 3 |
| 8 | nPr | Si(CH$_3$)$_3$ | H | H | Solid | 331 | 1 |
| 9 | nPr | SitBuMe$_2$ | H | H | 140° | 373 | 12 |
| 10 | n-Pr | CONHMe | H | H | 206° | 316 | 13 |
| 11 | t-Bu | Si(Me)$_3$ | H | H |  | 345 | 1 |
| 12 | t-Bu | CH$_2$OMe | H | H | 161–3° | 317 | 3 |
| 13 | Et | Si(Me)$_3$ | H | H | solid | 317 | 1 |
| 14 | n-Pr | Si(Me)$_3$ | H | Cl | solid | 365 | 1 |
| 15 | n-Pr | n-Pr | H | H | solid | 301 | 3 |
| 16 | n-Pr | CH$_2$OMe | H | Cl | solid | 337 | 3 |
| 17 | n-Pr | SiMe$_3$ | H | NO$_2$ | solid | 376 | 1 |
| 18 | c.hexyl | CH$_2$OMe | H | H | 171° | 343 | 3 |
| 19 | n-Pr | CO$_2$Me | H | H | 176° | 317 | 2 |

-continued

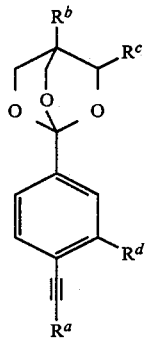

| Compound Number | $R^b$ | $R^a$ | $R^c$ | $R^d$ | M.pt | Mass Spectrum Chemical Ionisation M + 1 | Example |
|---|---|---|---|---|---|---|---|
| 20 | c.hexyl | SiMe$_3$ | H | H | 225° | 371 | 1 |
| 21 | n-Pr | CH$_2$OEt | H | H | solid | 317 | 3 |
| 22 | n-Pr | CH$_2$CH$_2$—OMe | H | H | solid | 317 | 3 |
| 23 | i-Bu | SiMe$_3$ | H | H | 149.0° | 345 | 1 |
| 24 | i-Bu | CH$_2$OMe | H | H | 103.5° | 317 | 3 |
| 25 | n-Pr | CH$_2$NH—COMe | H | H | solid | 330 | 3 |
| 26 | n-Bu | SiMe$_3$ | H | H | 128.6° | 345 | 1 |
| 27 | n-Bu | CH$_2$OMe | H | H | 104.8° | 317 | 3 |
| 28 | n-Pent. | SiMe$_3$ | H | H | 166.3° | 359 | 1 |
| 29 | n-Pent. | CH$_2$OMe | H | H | 120.7° | 331 | 3 |
| 30 | n-Pr | CH$_2$OAc | H | H | 98° | 330(M$^+$e.i.) | 7 |
| 31 | 2,2-di-Methyl-propyl | CH$_2$OMe | H | H | solid | 331 | 5 |
| 32 | 2,2-di-Methyl-propyl | SiMe$_3$ | H | H | solid | 359 | 5 |
| 33 | n-Pr | Me | H | H | solid | 273 | 8 |
| 34 | n-Pr | CH$_2$OCO—NHMe | H | H | 136.2 | 346 | 6 |
| 35 | n-Pr | CH$_2$OMe | CF$_3$ | H | solid | 371 | 4 |
| 36 | n-Pr | CH$_2$OMe | CN | H | 85° | 328 | 9 |
| 37 | Et | H | H | H | solid | 245 | 1 + 2 |
| 38 | n-Pr | H | H | H | solid | 259 | 1 + 2 |
| 39 | n-Bu | H | H | H | 90° | 273 | 1 + 2 |
| 40 | i-Bu | H | H | H | 122.5° | 273 | 1 + 2 |
| 41 | n-Pent. | H | H | H | 91.5° | 287 | 1 + 2 |
| 42 | 2,2-dimethyl-propyl | H | H | H | solid | 287 | 1 + 2 |
| 43 | n-Pr | H | H | Cl | solid | 293 | 1 + 2 |
| 44 | n-Pr | H | H | NO$_2$ | solid | 304 | 1 + 2 |
| 45 | n-Pr | CSNHMe | H | H | solid decomposes on heating | 332 | 13 |
| 46 | n-Pr | CH$_2$OSO$_2$—Me | H | H | solid | 367 | 14 |
| 47 | n-Bu | CH$_2$OMe | CF$_3$ | H | solid | 385 | 4 |
| 48 | t-Bu | SiMe$_3$ | H | H | | 345 | 1 |
| 49 | Ph | H | H | H | 196-197° | 293 | 1 + 2 |
| 50 | Ph | SiMe$_3$ | H | H | 220-222° | | 1 |
| 51 | C.hex | H | H | H | 190-192° | 299 | 11 |
| 52 | t-Bu | H | H | H | 167-168 | 272 | 11 |
| 53 | n-Pr | CONMe$_2$ | H | H | waxy solid | 330 | 7 |
| 54 | n-Pr | CSNMe$_2$ | H | H | 155° | 346 | 7 |
| 55 | n-Pr | CH$_2$SEt | H | H | solid | 333 | 15 |
| 56 | n-Pr | CH$_2$SOEt | H | H | solid | | 16 |
| 57 | n-Pr | SMe | H | H | solid | 305 | 12 |
| 58 | n-Pr | SOMe | H | H | solid | 321 | 16 |

| NUCLEAR MAGNETIC RESONANCE SPECTRUM ($^1$H CARRIED OUT IN CDCl$_3$ AND EXPRESSED AS ppm FROM TMS, NUMBER OF PROTONS, NUMBER OF PEAKS, $J_{Hz}$ (WHERE APPROPRIATE) | |
|---|---|
| NUMBER | |
| 1 | 7.60, 4H, s; 4.3, 2H, q, 7; 4.1, 6H, s; 1.75, 3H, t, 7; 1.6–0.7, 5H, m. |
| 2 | 7.5, 4H, m; 4.35, 2H, s; 4.1, 6H, s; 3.5, 3H, s; 1.5–0.8, 7H, m. |
| 3 | 7.55, 2H, d, 8; 7.35, 2H, d, 8; 4.45, 2H, br.s; 4.1, 6H, s; 1.4–0.8, 7H, m. |

| NUCLEAR MAGNETIC RESONANCE SPECTRUM ($^1$H CARRIED OUT IN $CDCl_3$ AND EXPRESSED AS ppm FROM TMS, NUMBER OF PROTONS, NUMBER OF PEAKS, $J_{Hz}$ WHERE APPROPRIATE) | |
|---|---|
| NUMBER | |
| 4 | 7.7–7.1, 9H, m; 4.1, 6H, s; 1.4–0.8; 7H, m |
| 5 | 7.55, 2H, d, 8; 7.35, 2H, d, 8; 4.1, 6H, s; 1.4, 9H, s; 1.4–0.8, 7H, m. |
| 6 | 7.45, 2H, d, 8; 7.20, 2H, d, 8; 4.1, 6H, s; 1.65, 6H, s; 1.4–0.8, 7H, m. |
| 7 | 7.55, 2H, d, 8; 7.35, 2H, d, 8; 4.1, 6H, s; 3.8, 2H, m; 2.7, 2H, t, 4; 1.7, 1H, t, 4; 1.35–1.15, 4H, m; 0.95, 3H, br.t, 5 |
| 8 | 7.40, 4H, m; 4.1, 6H, s; 1.4–0.8, 7H, m; 0.3, 9H, s. |
| 12 | 7.60, 2H, d, 7; 7.45, 2H, d, 7; 4.80, 2H, s; 4.20, 6H, s; 3.45, 3H, s; 0.90, 9H, s. |
| 13 | 7.50, 4H, m; 4.10, 6H, s; 1.60–0.80, 5H, m; 0.30, 9H, s. |
| 14 | 7.80, 1H, m; 7.50, 2H, m; 4.20, 6H, s; 1.50–0.80, 7H, m; 0.30, 9H, s. |
| 9 | 7.50, 4H, m; 4.10, 6H, s; 1.60–0.80, 16H, m; 0.20, 6H, s. |
| 10 | 7.60, 2H, d, 6; 7.50, 2H, d, 6; 5.90, 1H, s(broad); 4.10, 6H, s; 2.90, 3H, d, 6; 1.25, 4H, m; 0.95, 3H, t. |
| 15 | 7.55, 2H, d, 7; 7.35, 2H, d, 7; 4.10, 6H, s; 2.35, 2H, t, 7; 1.60–0.80, 12H, m. |
| 16 | 7.70, 1H, m; 7.50, 2H, m; 4.40, 2H, s; 4.20, 6H, s; 3.50, 3H, s; 1.50–0.90, 7H, m. |
| 17 | 8.30, 1H, m; 7.70, 2H, m; 4.20, 6H, s; 1.50–0.80, 7H, m; 0.25, 9H, s. |
| 18 | 7.45, 4H, m; 4.40, 2H, s; 4.20, 6H, s; 3.45, 3H, s; 2.00–0.80, 11H, m. |
| 19 | 7.65, 2H, d, 7; 7.45, 2H, d, 7; 4.10, 6H, s; 3.80, 3H, s; 1.25, 4H, m; 0.95, 3H, t, 7. |
| 20 | 7.55, 2H, d, 7; 7.45, 2H, d, 7; 4.10, 6H, s; 1.90–0.90, 11H, m; 0.25, 9H, s. |
| 21 | 7.50, 4H, m; 4.40, 2H, s; 4.10, 6H, s; 3.65, 2H, q, 6; 1.50–0.90, 10H, m. |
| 22 | 7.40, 4H, m; 4.10, 6H, s; 3.60, 2H, t, 6; 3.40, 3H, s; 2.65, 2H, t, 6; 1.40–0.80, 7H, m. |
| 23 | 7.55, 2H, d, 7; 7.45, 2H, d, 7; 4.10, 6H, s; 1.70, 1H, m; 1.5, 2H, d, 7; 0.95, 6H, d, 7. |
| 24 | 7.50, 4H, m; 4.40, 2H, s; 4.20, 6H, s; 3.60, 3H, s; 1.80, 1H, m; 1.15, 2H, d, 7; 1.05, 6H, d, 7. |
| 25 | 7.50, 2H, d, 7; 7.30, 2H, d, 7; 6.10, 1H, broad; 4.20, 2H, d, 6; 4.10, 6H, s; 2.00 3H, s; 1.40–0.80, 7H, m. |
| 26 | 7.55, 2H, d, 7; 7.45, 2H, d, 7; 4.15, 6H, s; 1.30, 6H, m; 0.95, 3H, t.6; 0.30, 9H, s. |
| 27 | 7.55, 2H, d, 7; 7.45, 2H, d, 7; 4.30, 2H, s; 4.10, 6H, s; 3.50, 3H, s; 1.30, 6H, m; 0.95, 3H, t, 6. |
| 28 | 7.55, 2H, d, 7; 7.45, 2H, d, 7; 4.10, 6H, s; 1.25, 8H, m; 0.90, 3H, t, 6; 0.25, 9H, s. |
| 29 | 7.55, 2H, d, 7; 7.45, 2H, d, 7; 4.30, 2H, s; 4.10, 6H, s; 3.45, 3H, s; 1.25, 8H, m; 0.90, 3H, t, 6. |
| 30 | 7.40, 4H, m; 4.85, 2H, s; 4.05, 6H, s; 2.10, 3H, s; 1.40–0.80, 7H, m. |
| 31 | 7.55, 2H, d, 7; 7.45, 2H, d, 7; 4.30, 2H, s; 4.20, 6H, s; 3.45, 3H, s; 1.25, 2H, s; 1.00, 9H, s. |
| 32 | 7.55, 2H, d, 7; 7.45, 2H, d, 7; 4.20, 6H, s; 1.25, 2H, s; 1.00, 9H, s; 0.25, 9H, s. |
| 33 | 7.55, 2H, d, 7; 7.40, 2H, d, 7; 4.10, 6H, s; 2.05, 3H, s; 1.25, 4H, m; 0.95, 3H, m. |
| 34 | 7.65, 4H, m; 5.10, 2H, s; 4.15; 6H, s; 2.95, 3H, d, 6; 1.60–0.80, 7H, m. |
| 35 | 7.60, 2H, d, 7; 7.40, 2H, d, 7; 4.50, 1H, m; 4.40, 1H, m; 4.35, 2H, s; 4.10, 3H, m; 3.45, 3H, s; 1.60–1.20, 4H, m; 0.95, 3H, t, 6. |
| 36 | 7.50, 4H, m; 5.00, 1H, d, 2; 4.50–4.00, 6H m; 3.50, 3H, s; 1.60–0.90, 7H, m. |
| 37 | 7.50, 4H, m; 4.10, 6H, s; 3.05, 1H, s; 1.60–0.80, 5H, m. |
| 38 | 7.50, 4H, m; 4.10, 6H, s; 3.05, 1H, s; 1.40–0.80, 7H, m. |
| 39 | 7.60, 2H, d, 7; 7.40, 2H, d; 4.10, 6H, s; 3.05, 1H, s; 1.30, 6H, m; 0.90, 3H, t, 7. |
| 40 | 7.60, 2H, d, 7; 7.45, 2H, d, 7; 4.10, 6H, s; 3.10, 1H, s; 1.70, 1H, m; 1.15, 2H, d, 6; 0.95, 6H, d, 6. |
| 41 | 7.60, 2H, d, 7; 7.45, 2H, d, 7; 4.10, 6H, s; 3.10, 1H, s; 1.30, 8H, m; 0.95, 3H, t, 6. |
| 42 | 7.55, 2H, d, 7; 7.40, 2H, d, 7; 4.20, 6H, s; 3.10, 1H, s; 1.25, 2H, s; 1.00, 9H, s. |
| 43 | 7.70, 1H, m; 7.50, 2H, m; 4.20, 6H, s; 3.40, 1H, s; 1.25, 4H, m; 0.95, 3H, t, 6. |
| 44 | 8.30, 1H, s; 7.80, 1H, d, 7; 7.65, 1H, d, 7; 4.10, 6H, s; 3.55, 1H, s; 1.30, 4H, m; 0.95, 3H, m. |
| 45 | 7.60, 2H, d, 6; 7.50, 2H, d, 6; 4.15, 6H, s; 3.25, 3H, d, 6; 1.25, 4H, m; 0.95, 3H, t, 6. |
| 46 | 7.60, 2H, d, 6; 7.50, 2H, d, 6; 5.10, 2H, s; 4.10, 6H, s; 3.15, 3H, s; 1.15, 4H, m, 0.95, 3H, m. |
| 47 | 7.60, 2H, d, 6; 7.45, 2H, d, 6; 4.50, 1H, m; 4.35, 3H, m; 4.10, 3H, m; 3.45, 3H, s; 1.30, 6H, m; 0.90, 3H, m. |
| 48 | 7.55–7.40, 4H, q; 4.15, 6H, s; 0.90, 9H, s; 0.20, 9H, s. |
| 49 | 7.65–7.15, 9H, m; 4.50, 6H, s; 3.10, 1H, s. |
| 50 | 7.60–7.15, 9H, m; 4.50, 6H, s; 0.25, 9H, s. |
| 51 | 7.55, 2H, d; 7.45, 2H, d; 4.1, 6H, s; 3.05, 1H, s; 0.9–1.6, and 1.3–0.9, 11H. |
| 52 | 7.55, 2H d; 7.45, 2H, d; 4.15, 6H, s; 3.05, 1H, s; 0.9, 9H, s. |
| 53 | 7.60, 2H, d, 7; 7.50, 2H, d, 7; 4.10, 6H, s; 3.30, 3H, s; 3.05, 3H, s; 1.25, 4H, m; 0.95, 3H, m. |
| 54 | 7.40, 4H, m; 3.95, 6H, s; 3.40, 3H, s; 3.30, 3H, s; 1.10, 4H, m; 0.80, 3H, m. |
| 55 | 7.55, 2H, d, 7; 7.40, 2H, d, 7; 4.10, 6H, s; 3.50, 2H, s; 2.80, 2H, q, 6; 1.35, 3H, t, 6; 1.25, 4H, m; 0.95, 3H, m. |
| 56 | 7.60, 2H, d, 7; 7.45, 2H, d, 7; 4.10, 6H, s; 3.80, 2H, m; 3.00, 2H, m; 1.40, 3H, t, 6; 1.30, 4H, m; 0.95, 3H, m. |
| 57 | 7.55, 2H, d, 7; 7.40, 2H, d, 7; 4.10, 6H, s; 2.50, 3H, s; 1.25, 4H, m; 0.95, 3H, m. |
| 58 | 7.65, 2H, d, 7; 7.50, 2H, d, 7; 4.10, 6H, s; 3.05, 3H, s; 1.25, 4H, m; 0.95, 3H, m |

(ii) BIOLOGICAL ACTIVITY

A. Lethal Activity Against Houseflies

The activity of compounds of the invention against unanaesthetised female *Musca domestica* (WRL strain), was demonstrated by the topical application to the test insect of a solution of the compound under test in butanone.

The activity of the test compound was also assessed when applied topically in conjun ction with the synergist piperonyl butoxide (6 μg piperonyl butoxide (PB) per insect). Mortality was assessed after 24 and 48 hours.

The following compounds were active at less than 30 μg/fly: 1,2,3,13,14,15,16,17,19,20,21,22,23,26,27

The following compounds were active at less than 1 μg/fly: 8, 11

B. Lethal Activity Against *Blattella germanica*

The activity of compounds of the invention against anaesthetised male *Blattella germanica* (WRL strain) was demonstrated by the topical application to the test insect of a solution of the compound under test in butanone.

The activity of the test compound was assessed when applied topically in conjunction with the synergist piperonyl butoxide(10 μg piperonyl butoxide per insect). Mortality was assessed after 24 and 48 hours.

The following compounds were active at less than 50 μg/insect: 1,7,8,11,13,17,20

The following compounds were active at less than 5 μg/insect: 2,3,15,16,19,21

C. Lethal Activity Against *Sitophilus granarius*

The activity of the compounds of the invention against *S.granarius* adults was demonstrated by addition of the compound in acetone solution to grain, to which the insects were later infested. Mortality was assessed after 6 days.

The following compounds gave activity at less than 200 ppm solution of acetone: 8,11,15,20,21,22,23,26.

The following compounds gave activity at less than 50 ppm solution of acetone: 2,14,16,19,27.

D. Lethal Activity Against *Culex quinquefasciatus*

The activity of the compounds of the invention against female Culex adults was demonstrated by direct spraying of 0.5 ml of compound in OPD/Methylene chloride. Mortality was assessed after 24 hours.

The following compounds were active at less than 1.0% 1,14,19,21,23,26,27

E. Mammalian Toxicity

Compound 2 has an $LD_{50}$ value of approximately 20 mg/kg when given orally to mice (Charles River CD1).

Compound 4 has an $LD_{50}$ value of greater than 200 mg/kg when given orally to mice (Charles River CD1).

| Formulations | |
|---|---:|
| 1. Emulsifiable Concentrate | |
| Compound of formula (I) | 10.00 |
| Ethylan KEO | 20.00 |
| Xylene | 67.50 |
| Butylated Hydroxyanisole | 2.50 |
| | 100.00 |
| 2. Wettable Powder | |
| Compound of formula (I) | 25.0 |
| Attapulgite | 69.50 |
| Sodium isopropylbenzene sulphonate | 0.50 |
| Sodium salt of condensed naphthalene sulphonic acid | 2.50 |
| Butylated hydroxytoluene | 2.50 |
| | 100.00 |
| 3. Dust | |
| Compound of formula (I) | 0.50 |
| Butylated Hydroxyanisole | 0.10 |
| Talc | 99.40 |
| | 100.00 |
| 4. Bait | |
| Compound of formula (I) | 40.25 |
| Icing Sugar | 59.65 |
| Butylated hydroxytoluene | 0.10 |
| | 100.00 |
| 5. Lacquer | |
| Compound of formula (I) | 2.5 |
| Resin | 5.0 |
| Butylated Hydroxyanisole | 0.5 |
| High aromatic white spirit | 92.0 |
| | 100.00 |
| 6. Aerosol | |
| Compound of formula (I) | 0.30 |
| Butylated Hydroxyanisole | 0.10 |
| 1,1,1-Trichloroethane | 4.00 |
| Odorless Kerosene | 15.60 |
| Arcton 11/12. 50:50 mix | 80.00 |
| | 100.00 |
| 7. Spray | |
| Compound of formula (I) | 0.1 |
| Butylated Hydroxyanisole | 0.1 |
| Xylene | 10.0 |
| Odorless Kerosene | 89.8 |
| | 100.00 |
| 8. Potentiated Spray | |
| Compound of formula (I) | 0.1 |
| Piperonyl Butoxide | 0.5 |
| Butylated Hydroxyanisole | 0.1 |
| Xylene | 10.1 |
| Odorless Kerosene | 89.2 |
| | 100.0 |

We claim:
1. A compound of the formula:

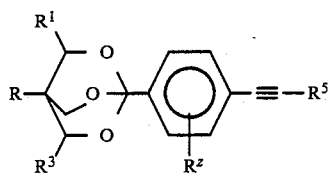

wherein

R is $C_{2-4}$ alkyl, alkenyl or alkynyl, or $C_{2-10}$ alkyl, alkenyl or alkynyl substituted by cyano, halo, $C_{3-4}$ cycloalkyl, $C_{1-4}$ alkoxy, or a group $S(O)_m R^4$ where $R^4$ is $C_{1-4}$ alkyl or phenyl, each optionally substituted by $C_{1-4}$ alkoxy, $C_{1-3}$ alkyl, $C_{2-4}$ alkynyl, halo, cyano or a group $S(O)_m R^4$ as defined above;

$R^1$ and $R^3$, which are the same or different, are each hydrogen, halo, $C_{1-3}$ alkyl, $C_{2-3}$ alkenyl or alkynyl, the alkyl, alkenyl or alkynyl each substituted by halo, cyano or a group $C_{1-4}$ alkoxy; alkyl carbalkoxy containing up to 6 carbon atoms, a group $S(O)_m R^4$ as defined above or alkynyl substituted by tri-$C_{1-4}$ alkysilyl, or $R^1$ is COO-$C_{1-4}$-alkyl, cyano, gem-dimethyl, gem-dicyano, gem-dihalo, gem-diethynyl, spirocyclopropyl, spiro-oxirane or spiro-oxetane, substituted spiro-oxirane or spiro-oxetane, oxo or methylene optionally substituted by cyano or halo or —$CF_3$ or $R^1$ and R and the carbon atoms to which they are attached from a $C_{5-7}$ carbocyclic ring or a carbocyclic ring substituted by $C_{1-3}$ alkyl, $C_{1-3}$ alkoxy or $C_{2-3}$ alkenyl;

$R^z$ is 1 to 4 groups each selected from hydrogen, halo, cyano, azido, nitro, $C_{1-3}$ alkyl or alkoxy, $C_{1-3}$ alkyl or alkoxy substituted by halo, $C_{2-3}$ alkenyl or alkynyl, or $C_{2-3}$ alkenyl or alkynyl substituted by halo; and $R^5$ is bromine, chlorine, iodine, a group $S(O)_m R^{4x}$ wherein $R^{4x}$ is trifluoromethyl or a group $R^4$ as defined above, methyl or ethyl optionally substituted by hydroxy, a group $OSO_2 R^{10x}$ wherein $R^{10x}$ is $C_{1-4}$ alkyl, phenyl or tolyl, $C_{1-4}$ alkoxy, $C_{1-4}$ acyloxy optionally substituted by an amino group mono or di substituted by $C_{1-4}$ alkyl groups or mono-substituted by phenyl optionally substituted by one to three halogen atoms, a group $NR^{11}R^{12}$ wherein $R^{11}$ is hydrogen or $C_{1-4}$ alkyl, $R^{12}$ is hydrogen, $C_{1-4}$ alkyl or a group COR$^{13}$ wherein $R^{13}$ is $C_{1-4}$ alkyl or alkoxy, a group CX.R$^6$ where X is oxygen or sulfur and $R^6$ is a $C_{1-6}$ hydrocarbyl or $C_{1-6}$ hydrocarbyloxy group optionally substituted by fluoro or an amino group optionally substituted by one or two $C_{1-4}$ alkyl groups or $R^5$ is cyano, or a silyl group substituted by three $C_{2-4}$ alkyl groups or two $C_{1-4}$ alkyl groups and a phenyl group.

2. A compound according to claim 1, in which R is n-propyl, n-butyl, i-butyl, t-butyl, or cyclohexyl.

3. A compound according to claim 1 in which $R^1$ is hydrogen, methyl, trifluoromethyl or cyano.

4. A compound according to claim 1 wherein $R^5$ is substituted methyl or substituted ethyl, the substituents being at least one hydroxy or methoxy group.

5. A compound according to claim 1 in which $R^3$ is hydrogen, methyl or trifluoromethyl.

6. A compound according to claim 1 which is
1-[3-nitro-4-(2-trimethylsilylethynyl)-phenyl]-4-n-propyl-2,6,7-trioxabicyclo[2,2,2]octane;
4-n-pentyl-1-[4-(2-trimethylsilylethynyl]-2,6,7-trioxabicyclo[2,2,2]octane;
1-[3-chloro-4-(2-trimethylsilylethynyl)phenyl]-2,6,7-trioxabicyclo[2,2,2]octane;
4-propyl-1-[4-(2-trimethylsilylethynyl)phenyl]-2,6,7-trioxabicyclo[2,2,2]octane;
1-[4-(3-methoxyprop-1-ynyl)phenyl]-4-propyl-2,6,7-trioxabicyclo[2,2,2]octane; -propyl-2,6,7-trioxabicyclo[2,2,2]octane;
4-n-butyl-1-[4-(2-trimethylsilylethynyl)phenyl]-2,6,7-trioxabicyclo-[2,2,2]octane;
4-i-butyl-1-[4-(2-trimethylsilylethynyl)phenyl]-2,6,7-trioxabicyclo-[2,2,2]octane;
1-[4-(3-ethoxyprop-1-ynyl)phenyl]-4-n-propyl-2,6,7-trioxabicyclo[2,2,2]octane;
4-methoxy-1-[4-(4-n-propyl-2,6,7-trioxabicyclo[2,2,2]oct-1-yl)phenyl]but-1-yne;
4-i-butyl-1-[4-(3-methoxyprop-1-ynyl-phenyl]-2,6,7-trioxabicyclo[2,2,2]octane;
N-[3-[4-(4-n-propyl-2,6,7-trioxabicyclo[2,2,2]oct-1-yl)phenyl]prop-2-ynyl]acetamide;
methyl 3-[4-(4-n-propyl-2,6,7-trioxabicyclo[2,2,2]oct-1-yl)-phenyl]prop-2-ynoate
4-cyclohexyl-1-(4-ethynylphenyl)-2,6,7-trioxabicyclo[2,2,2]octane;
4-t-butyl-1-[4-(3-methoxyprop-1-ynyl)phenyl]-2,6,7-trioxabicyclo-[2,2,2]octane;
1-[3-chloro-4-(3-methoxyprop-1-ynyl)phenyl]-4-n-propyl-2,6,7-trioxabicyclo[2,2,2]octane;
4-cyclohexyl-1-[4-(3-methoxyprop-1-ynyl)phenyl]-2,6,7-trioxabicyclo[2,2,2]octane;
4-n-butyl-1-[4-(3-methoxyprop-1-ynyl)phenyl]-2,6,7-trioxabicyclo[2,2,2]octane;
1-[4-(3-methoxyprop-1-ynyl)phenyl]-4-n-pentyl-2,6,7-trioxabicyclo[2,2,2]octane;
1-[4-(3-methoxyprop-1-ynyl)phenyl]-4-n-propyl-3-trifluoromethyl-2,6,7-trioxabicyclo[2,2,2]octane;
3-cyano-1-[4-(3-methoxyprop-1-ynyl)phenyl]-4-n-propyl-2,6,7-trioxabicyclo[2,2,2]octane;
4-(2,2-dimethylpropyl)-1-[4-(3-methoxyprop-1-yl)phenyl]-2,6,7-trioxabicyclo[2,2,2]octane;
4-(2,2-dimethylpropyl)-1-[4-(2-trimethylsilylethynyl)-phenyl]2,6,7-trioxabicyclo[2,2,2]octane;
N-methyl-3-[4-(4-n-propyl-2,6,7-trioxabicyclo[2,2,2]oct-1-yl)phenyl]prop-2-ynyl carbamate;
3-[4-(4-n-propyl-2,6,7-trioxabicyclo[2,2,2]octyl)-phenyl]prop-2-yn-1-ol;
3-[4-(4-n-propyl-2,6,7-trioxabicyclo[2,2,2]oct-1-yl)phenyl]prop-2-ynyl acetate;
4-n-propyl-1-[4-(prop-1-ynyl)-phenyl]-2,6,7-thiabicyclo[2,2,2]octane;
1-[4-(2-t-butyldimethylsilylethynyl)phenyl]-4-n-propyl-2,6,7-trioxabicyclo[2,2,2]octane;
4-n-butyl-1-[4-(3-methoxyprop-1-ynyl)phenyl]-3-trifluoromethyl-2,6,7-trioxabicyclo[2,2,2]octane;
4-t-butyl-1-[4-(2-trimethylsilylethynyl)phenyl]-2,6,7-trioxabicyclo[2,2,2]octane;
4-cyclohexyl-1-[4-(2-trimethylsilylethynyl)phenyl]-2,6,7-trioxabicyclo[2,2,2]octane;
1-[4-(pent-1-ynyl)phenyl]-4-n-propyl-2,6,7-trioxabicyclo[2,2,2]octane;
4-Phenyl-1-[4-(2-trimethylsilylethynylphenyl)]2,6,7-trioxabicyclo[2,2,2]octane.

7. A compound of the formula IA:

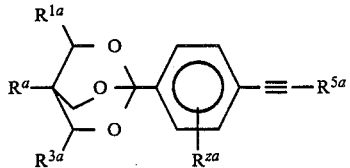

wherein
$R^a$ is $C_{2-7}$ alkyl, alkenyl or alkynyl, each optionally substituted by cyano, halogen or $C_{1-4}$ alkoxy, or $R^a$ is $C_{3-10}$ cycloalkyl, $C_{4-10}$ cycloalkenyl or phenyl, each optionally substituted by $C_{1-4}$ alkoxy, $C_{1-3}$ alkyl, $C_{2-4}$ alkynyl, halogen or cyano;
$R^{1a}$ is hydrogen, $C_{1-3}$ alkyl, $C_{2-3}$ alkenyl or alkynyl each optionally substituted by cyano, $C_{1-4}$ alkoxy, $C_{1-4}$ alkylthio, alkyl carbalkoxy containing up to 6 carbon atoms or halo, or $R^{1a}$ is cyano, gem-dimethyl or $R^{1a}$ and $R^a$ and the carbon atoms to which they are attached form a $C_{5-7}$ carbocyclic ring or a carbocyclic ring substituted by $C_{1-3}$ alkyl, or $C_{2-3}$ alkoxy or alkenyl;
$R^{za}$ is 1 to 4 groups each selected from hydrogen, halo, cyano, azido, nitro, $C_{1-3}$ alkyl or alkoxy, $C_{1-3}$ alkyl or alkoxy substituted by halo, $C_{2-3}$ alkenyl or alkynyl, or $C_{2-3}$ alkenyl or alkynyl substituted by halo; and
$R^{5a}$ is methyl or ethyl substituted by hydroxy, a group $OSO_2R^{10x}$ wherein $R^{10x}$ is alkyl, phenyl or tolyl, $C_{1-4}$ alkoxy, $C_{1-4}$ acyloxy optionally substituted by an amino group mono or di substituted by $C_{1-4}$ alkyl groups or mono-substituted by phenyl optionally substituted by one to three halogen atoms, a group $NR^{11}R^{12}$ wherein $R^{11}$ is hydrogen or $C_{1-4}$ alkyl, $R^{12}$ is hydrogen, $C_{1-4}$ alkyl or a group $COR^{13}$ wherein $R^{13}$ is $C_{1-4}$ alkyl or alkoxy, a group $-CO.R^{6a}$ where $R^{6a}$ is a $C_{1-6}$ hydrocarbyl or $C_{1-6}$ hydrocarbyloxy group or an amino group optionally substituted by one or two $C_{1-4}$ alkyl groups or $R^{5a}$ is cyano, or a silyl group substituted by three $C_{2-4}$ alkyl groups or two $C_{1-4}$ alkyl groups and a phenyl group; and
$R^{3a}$ is hydrogen, $C_{1-3}$ alkyl, $C_{2-3}$ alkenyl or alkynyl each optionally substituted by cyano, $C_{1-4}$ alkylthio, $C_{1-4}$ alkoxy or halo.

8. An insecticidal or acaricidal composition comprising an insecticidally or acaricidally effective amount of a compound of formula (I) as defined in claim 1 in admixture with a carrier or diluent.

9. A method for the control of pests comprising application to the pest or to an environment susceptible to pest infestation of a pesticidally effective amount of a compound according to claim 1 a composition or mixture according to claim 1 or 7.

* * * * *